(12) United States Patent
Pages et al.

(10) Patent No.: US 11,426,462 B2
(45) Date of Patent: Aug. 30, 2022

(54) MONOVALENT ANTI-CD3 ADJUVANTS

(71) Applicant: Mayo Foundation for Medical Education and Research, Rochester, MN (US)

(72) Inventors: Diana Gil Pages, Rochester, MN (US); Adam G. Schrum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 883 days.

(21) Appl. No.: 15/943,420

(22) Filed: Apr. 2, 2018

(65) Prior Publication Data

US 2018/0221471 A1   Aug. 9, 2018

Related U.S. Application Data

(63) Continuation of application No. 15/426,745, filed on Feb. 7, 2017, now abandoned, which is a continuation of application No. 14/571,601, filed on Dec. 16, 2014, now abandoned.

(60) Provisional application No. 61/918,545, filed on Dec. 19, 2013.

(51) Int. Cl.
*C07K 16/28* (2006.01)
*A61K 39/39* (2006.01)
*A61K 39/00* (2006.01)
*A61K 39/395* (2006.01)

(52) U.S. Cl.
CPC .......... *A61K 39/39* (2013.01); *A61K 39/0011* (2013.01); *A61K 39/3955* (2013.01); *A61K 39/39558* (2013.01); *C07K 16/2809* (2013.01); *A61K 2039/505* (2013.01); *A61K 2039/5158* (2013.01); *A61K 2039/55516* (2013.01); *A61K 2039/55533* (2013.01); *C07K 2317/21* (2013.01); *C07K 2317/24* (2013.01); *C07K 2317/35* (2013.01); *C07K 2317/55* (2013.01); *C07K 2317/75* (2013.01)

(58) Field of Classification Search
None
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 5,821,337 A | 10/1998 | Carter |
| 6,093,381 A | 7/2000 | Triozzi et al. |
| 6,113,901 A | 9/2000 | Bluestone |
| 6,406,696 B1 | 6/2002 | Bluestone |
| 6,462,189 B1 | 10/2002 | Koide |
| 6,491,916 B1 | 12/2002 | Bluestone et al. |
| 6,673,901 B2 | 1/2004 | Koide |
| 7,119,171 B2 | 10/2006 | Koide |
| 7,598,352 B2 | 10/2009 | Koide |
| 7,728,114 B2 | 6/2010 | Mach et al. |
| 2003/0165508 A1 | 9/2003 | Choi et al. |
| 2003/0216551 A1 | 11/2003 | Delovitch |
| 2008/0095766 A1 | 4/2008 | Koenig et al. |
| 2014/0141020 A1 | 5/2014 | Gil Pages et al. |

FOREIGN PATENT DOCUMENTS

| | | |
|---|---|---|
| EP | 1025854 | 8/2000 |
| EP | 1025855 | 8/2000 |
| WO | WO 1991/011465 | 8/1991 |
| WO | WO 2009/090656 | 7/2009 |
| WO | WO 2012/173819 | 12/2012 |
| WO | WO 2013/186613 | 12/2013 |

OTHER PUBLICATIONS

Meyer et al. (British Journal of Haematology, 2018, 180, 808-820). (Year: 2018).*
Lloyd et al. (Protein Engineering, Design & Selection vol. 22 No. 3 pp. 159-168, 2009). (Year: 2009).*
Edwards et al. (J. Mol. Biol. (2003) 334, 103-118). (Year: 2003).*
"Mechanisms and consequences of CD3 rearrangement during TCR triggering" [R01 application submitted in Oct. 2012 that was awarded in May 21, 2013].

(Continued)

*Primary Examiner* — Zachary S Skelding
(74) *Attorney, Agent, or Firm* — Stinson LLP

(57) ABSTRACT

This document provides methods and materials related to using monovalent anti-CD3 antibodies (e.g., monovalent anti-CD3 Fab fragments) as adjuvants to increase the immune response produced against an antigen (e.g., a tumor associated antigen). For example, vaccine compositions containing monovalent anti-CD3γε Fab fragments in combination with tumor associated antigens (e.g., tumor associated antigens having little or no immunogenicity in the absence of monovalent anti-CD3γε Fab fragments) alone or in combination with adjuvants for signals two and/or three required for full activation of T cell immune function, as well as methods and materials for using monovalent anti-CD3γε Fab fragments to increase the immune response produced against an antigen (e.g., a tumor associated antigen) within a mammal (e.g., a human) are provided.

9 Claims, 26 Drawing Sheets

(56) References Cited

OTHER PUBLICATIONS

Arnett et al., "Crystal structure of a human CD3-epsilon/delta dimer in complex with a UCHT1 single-chain antibody fragment," *Proc Natl Acad Sci U S A.*, 1(46):16268-16273, Epub Nov. 8, 2004.
Baines and Thorpe, "Purification of immunoglobulin g (IgG)," *Methods Mol Biol.*, 10:79-104, 1992.
Barbas III and Lerner, "Combinatorial immunoglobulin libraries on the surface of phage (Phabs): Rapid selection of antigen-specific fabs," *Methods*, 2(2):119-124, Apr. 1991.
Blazar et al., "In vivo or in vitro anti-CD3 epsilon chain monoclonal antibody therapy for the prevention of lethal murine graft-versus-host disease across the major histocompatibility barrier in mice," *J Immunol.*, 152(7):3665-3674, Apr. 1, 1994.
Bloom et al., "FN3: a new protein scaffold reaches the clinic," *Drug Discov Today*, 14(19-20):949-955, Epub Jul. 2, 2009.
Boder et al., "Yeast surface display for screening combinatorial polypeptide libraries," *Nat Biotechnol.*, 15(6):553-557, Jun. 1997.
Carter et al., "Humanization of an anti-p185HER2 antibody for human cancer therapy," *Proc Natl Acad Sci U S A.*, 89(10):4285-4289, May 15, 1992.
Chatenoud, "Anti-CD3 antibodies: towards clinical antigen-specific immunomodulation," *Curr Opin Pharmacol.*, 4(4):403-407, Aug. 2004.
Coulie et al., "Identification of a murine monoclonal antibody specific for an allotypic determinant on mouse CD3," *Eur J Immunol.*, 21(7):1703-1709, Jul. 1991.
Dall'Acqua et al., "Antibody humanization by framework shuffling," *Methods*, 36(1):43-60, May 2005.
Damschroder et al., "Framework shuffling of antibodies to reduce immunogenicity and manipulate functional and biophysical properties," *Mol Immunol.*, 44(11):3049-3060, Epub Jan. 22, 2007.
Ellenhorn et al., "Mechanism of tumor rejection in anti-CD3 monoclonal antibody-treated mice," *J Immunol.*, 144(7):2840-2846, Apr, 1, 1990.
European Office Action in international Application No. 12800018.9, dated Feb. 23, 2018, 6 pages.
European Search Report for Application No. 12800018,9, dated Dec. 23, 2014, 5 pages.
Finkelstein et al., "Bedside to bench and back again: how animal models are guiding the development of new immunotherapies for cancer," *J Leukoc Biol.*, 76(2):333-337, Epub May 20, 2004.
GenBank NCBI Accession No. NP_000064.1; GI 4557429, "T-cell surface glycoprotein CD3 gamma chain precursor [*Homo sapiens*]," Jan, 8, 2016, 3 pages.
GenBank NCBI Accession No. NP_000723.1; GI 4502669, "T-cell surface glycoprotein CD3 delta chain isoform A precursor [*Homo sapiens*]," Jan. 8, 2016, 3 pages.
GenBank NCBI Accession No. NP_000724.1; GI 4502671, "T-cell surface glycoprotein CD3 epsilon chain precursor [*Homo sapiens*]," Jan. 8, 2016, 4 pages.
Gil et al., "A role for CD8 in the developmental tuning of antigen recognition and CD3 conformational change," *J Immunol.*, 180(6):3900-3909, Mar. 15, 2008.
Gil et al., "Recruitment of Nek by CD3 epsilon reveals a ligand-induced conformational change essential for T cell receptor signaling and synapse formation," *Cell.*, 109(7):901-912, Jun. 28, 2002.
Gil et al., "T cell receptor engagement by peptide-MHC ligands induces a conformational change in the CD3 complex of thymocytes," *J Exp Med.*, 201(4):517-522, Feb. 21, 2005.
Gil Pages, "Project Summary/Abstract," for project titled, "Mechanisms and consequences of CD3 rearrangement during TCR triggering," Grant No. 1R01AI097187-01A1, ERA Commons, grant awarded May 21, 2013, 1 page.
Gil, "Impact of conformational changes on the function of antigen receptors," Molecular Microbiology and Immunology Seminar Series, University of Missouri, Columbia, School of Medicine, Columbia, Missouri, Apr. 4, 2013 [oral presentation].
Green and Manson, "Production of Polyclonal Antisera," *Immunochemical Protocols*, Methods in Molecular Biology™ 10:1-5, 1992.

Green et al., "Antigen-specific human monoclonal antibodies from mice engineered with human Ig heavy and light chain YACs," *Nat Genet*, 7(1):13-21, May 1994.
Gribskov et al., "The codon preference plot: graphic analysis of protein coding sequences and prediction of gene expression," *Nucleic Acids Res.*, 12(1 Pt 2):539-549, Jan. 11, 1984.
Griffiths et al., "Isolation of high affinity human antibodies directly from large synthetic repertoires," *EMBO J.*, 13(14):3245-3260, Jul. 15, 1994.
Grosse-Hovest et al., "Tumor-growth inhibition with bispecific antibody fragments in a syngeneic mouse melanoma model: The Role of targeted T-cell co-stimulation via CD28," *J Canc.*, 80(1):138-144, Jan. 5, 1999.
Hackel et al., "Stability and CDR composition biases enrich binder functionality landscapes," *J Mol Biol.*, 401(1):84-96, Epub Jun. 9, 2010.
Harlow et al., "Antibody Response," & "Immunizations," *Antibodies, A Laboratory Manual*, Chpt. 4, pp. 37-47, Chpt. 5, pp. 53-59, 1988.
Hirsch et al., "Effects of in vivo administration of anti-CD3 monoclonal antibody on T cell function in mice. II. In vivo activation of T cells," *J Immunol.*, 142(3):737-743, Feb. 1, 1989.
Hirsch et al., "In vivo administration of anti-CD3 monoclonal antibody can activate immune responses thus preventing malignant tumor growth," *Princess Takamatsu Symp.*, 19:237-243, 1988.
Hoffmann, "Induction of CD3 Conformational Change increases T cell receptor reactivity towards weak antigens," Autumn Immunology Conference, Chicago, Illinois, 1 page [abstract], Nov. 22-25, 2013.
Hoffmann, "Manipulation of TCR Antigen recognition increases anti-tumor T cell function," Autumn Immunology Conference, Chicago, Illinois, 1 page, [poster] Nov. 22-25, 2013.
Huse et al., "Generation of a large combinatorial library of the immunoglobulin repertoire in phage lambda," *Science*, 246:1275-1281, Dec. 8, 1989.
Hwang et al., "Use of human germline genes in a CDR homology-based approach to antibody humanization," *Methods*, 36(1):35-42, May 2005.
International Preliminary Report on Patentability for PCT/US2012/040919, dated Jan. 3, 2014, 6 pages.
International Search Report and Written Opinion for PCT/US2012/040919, dated Feb. 1, 2013, 10 pages.
Jones et al., "Replacing the complementarity-determining regions in a human antibody with those from a mouse," *Nature*, 321(6069):522-525, May 29-Jun. 4, 1986.
Kashmiri et al., "SDR grafting-a new approach to antibody humanization," *Methods.*, 36(1):25-34, May 2005.
Kim et al., "The alphabeta T cell receptor is an anisotropic mechanosensor," *J Biol Chem.*, 284(45):31028-31037, Nov. 6, 2009.
Kjer-Nielsen et al., "Crystal structure of the human T cell receptor CD3 epsilon gamma heterodimer complexed to the therapeutic mAb OKT3," *Proc Natl Acad Sci U S A.*, 101(20):7675-7680, Epub May 10, 2004.
Knappik et al., "Fully synthetic human combinatorial antibody libraries (HuCAL) based on modular consensus frameworks and CDRs randomized with trinucleotides," *J Mol Biol.*, 296(1):57-86, Feb. 11, 2000.
Köhler and Milstein, "Continuous cultures of fused cells secreting antibody of predefined specificity," *Nature*, 256(5517):495-497, Aug. 7, 1975.
Koide and Koide, "Monobodies: antibody mimics based on the scaffold of the fibronectin type III domain," *Methods Mol Biol.*, 352:95-109, 2007.
Koide et al., "Design and Engineering of Synthetic Binding Proteins Using Nonantibody Scaffolds," *Protein Engineering and Design*, Chpt. 5, pp. 109-130, (CRC Press 2009).
Koide et al., "Probing protein conformational changes in living cells by using designer binding proteins: application to the estrogen receptor," *Proc Natl Acad Sci U S A.*, 99(3):1253-1258, Epub Jan. 29, 2002.
Koide et al., "Teaching an old scaffold new tricks: monobodies constructed using alternative surfaces of the FN3 scaffold," *J Mol Biol.*, 415(2):393-405, Jan. 13, 2012.

(56) References Cited

OTHER PUBLICATIONS

Koide et al., "The fibronectin type III domain as a scaffold for novel binding proteins," *J Mol Biol.*, 284(4):1141-1151, Dec. 11, 1998.
Kummer et al., "Increased in vivo mitogenicity of anti-TCR/CD3 monoclonal antibody through reduced interaction with Fcgamma receptors," Immunol Lett., 75(2): 153-158, Jan, 1, 2001.
Kung et al., "Monoclonal antibodies defining distinctive human T cell surface antigens," *Science*, 206(4416):347-349, Oct. 19, 1979.
Kunkel et al., "[19] Rapid and efficient site-specific mutagenesis without phenotypic selection," *Methods Enzymol.*, 154:367-382, 1987.
Lazar et al., "A molecular immunology approach to antibody humanization and functional optimization," *Mol. Immunol.*, 44(8):1986-1998, Epub Oct. 31, 2006.
Lonberg et al., "Antigen-specific human antibodies from mice comprising four distinct genetic modifications," *Nature*, 368(6474):856-859, Apr. 28, 1994.
Losman et al., "Baboon anti-idiotype antibodies mimic a carcinoembryonic antigen epitope," *Int J Cancer.*, 46(2):310-314, Aug. 15, 1990.
Mann et al., "Epitope-guided engineering of monobody binders for in vivo inhibition of Erk-2 signaling," *ACS Chem Biol.*, 8(3):608-616, Epub Dec. 18, 2012.
Marano et al., "Bivalent binding of an anti-CD3 antibody to Jurkat cells induces association of the T cell receptor complex with the cytoskeleton," *J Immunol.*, 143(3):931-938, Aug. 1, 1989.
Miescher et al., "Production and characterization of a rat monoclonal antibody against the murine CD3 molecular complex," *Immunol Lett*, 23:113-118, 1989/1990.
Nakajima et al., "Immunotherapy with anti-CD3 monoclonal antibodies and recombinant interleukin 2: stimulation of molecular programs of cytotoxic killer cells and induction of tumor regression," *Proc Natl Acad Sci U S A.*, 91(17):7889-7893, Aug. 16, 1994.
Nelson et al., "IgG Fab fragments forming bivalent complexes by a conformational mechanism that is reversible by osmolytes," *J Biol Chem.*, 287(51):42936-42950, Epub Oct. 29, 2012.
Nisonhoff et al., "Separation of univalent fragments from the bivalent rabbit antibody molecule by reduction of disulfide bonds," *Arch Biochem Biophys.*, 89:230-244, Aug. 1960.
Orlandi et al., "Cloning immunoglobulin variable domains for expression by the polymerase chain reaction," *Proc Natl Acad Sci U S A.*, 86(10):3833-3837, May 1989.
Pan et al., "Biochemical evidence for the presence of a single CD3delta and CD3gamma chain in the surface T cell receptor/CD3 complex," *J Biol Chem.*, 279(49):51068-51074, Epub Sep. 30, 2004.
Porter, "The hydrolysis of rabbit y-globulin and antibodies with crystalline papain," *Biochem J.*, 73:119-126, Sep. 1959.
Radar et al., "A phage display approach for rapid antibody humanization: designed combinatorial V gene libraries," *Proc Natl Acad Sci U S A.*, 95(15):8910-8915, Jul. 21, 1998.
Rader, "Overview on Concepts and Applications of Fab Antibody Fragments," *Current Protocols in Protein Science*, Unit 6,9, Suppl. 55, 14 pages, Feb. 2009.
Riechmann et al., "Reshaping human antibodies for therapy," *Nature*, 332(6162):323-327, Mar. 24, 1988.
Rosok et al., "A combinatorial library strategy for the rapid humanization of anticarcinoma BR96 Fab," *J Biol Chem.*, 271(37):22611-22618, Sep. 13, 1996.
Salmerón et al., "A conformational epitope expressed upon association of CD3-epsilon with either CD3-delta or CD3-gamma is the main target for recognition by anti-CD3 monoclonal antibodies," *J Immunol.*, 147(9):3047-3052, Nov. 1, 1991.
Sandhu, "Protein engineering of antibodies," *Crit Rev Biotechnol.*, 12(5-6)437-462, 1992.
Singer et al., "Optimal humanization of 1B4, an anti-CD18 murine monoclonal antibody, is achieved by correct choice of human V-region framework sequences," *J Immunol.*, 150(7):2844-2857, Apr. 1, 1993.
Sloan-Lancaster and Allen, "Altered peptide ligand-induced partial T cell activation: molecular mechanisms and role in T cell biology," *Annu Rev Immunol.*, 14:1-27, 1996.
Smans et al., "Bispecific antibody-mediated lysis of placental and germ cell alkaline phosphatase targeted solid tumors in immunocompetent mice," *Cancer Res.*, 55(19)4383-4390, Oct. 1, 1995.
Sun et al., "Mechanisms contributing to T cell receptor signaling and assembly revealed by the solution structure of an ectodomain fragment of the CD3 epsilon gamma heterodimer," *Cell*, 105(7):913-923, Jun. 29, 2001.
Taylor et al., "Human immunoglobulin transgenes undergo rearrangement, somatic mutation and class switching in mice that lack endogenous IgM," *Int Immunol.*, 6(4):579-591, Apr. 1994.
Verhoeyen et al., "Reshaping human antibodies: grafting an antilysozyme activity," *Science*, 239(4847):1534-1536, Mar. 25, 1988.
Wikipedia, "Monobody," Aug. 6, 2015, 5 pages.
Winter et al., "Making antibodies by phage display technology," *Annu Rev Immunol.*, 12:433-455, 1994.
Wojcik et al., "A potent and highly specific FN3 monobody inhibitor of the Abi SH2 domain," *Nat Struct Mol Biol.*, 17(4):519-527, Epub Mar. 28, 2010.
Ito et al., NOD/SCIDYC mouse: an excellent receipient mouse model for engrallmnent of human cells; Blood, 2002, vol. 100, No. 9, 8-pages.

* cited by examiner

Blocking CD3-PD of open CD3:
Assay background
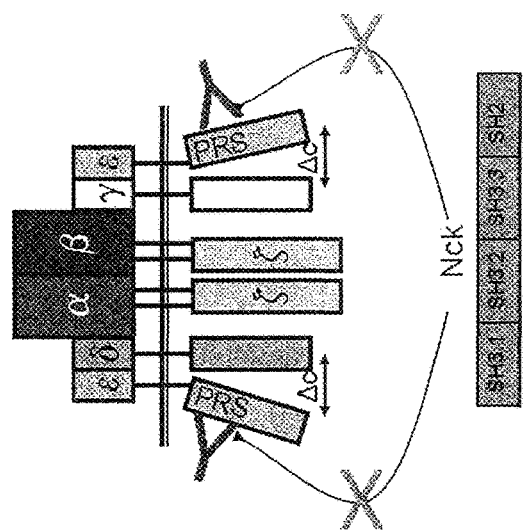
Binding of APA 1/1 to the cytoplasmic tail of epsilon blocks the pull down by Nck SH3.1
Stimulating CD3-PD to open CD3:
Maximum signal
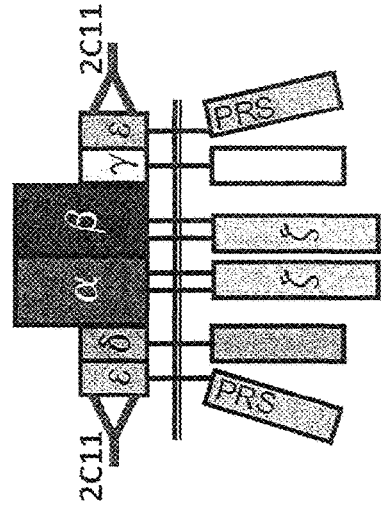
Binding of the extracellular domain by 2C11 causes the maximum amount (saturation) of conformational change
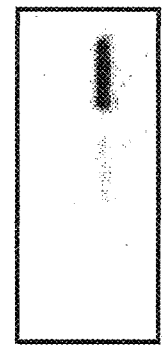 
Figure 4

CD3Δc Physical Properties
- Independent of Src kinase and other enzymatic activity
- Dependent on proteins within TCR/CD3
- Dependent on TCR/pMHC binding or anti-CD3mAb engagement Only strong/immunogenic antigens induce CD3Δc in Mature T cells

CD3Δc Functional Properties
- Required for full TCR/CD3 signaling
- Possible role in thymic selection
- Possible role in T cell proliferation

CD3ε PRS Functional Properties
- Role in TCR/CD3 expression, ubiquitination, and degradation
- Role in efficiency of thymocyte development
- Role in synapse formation

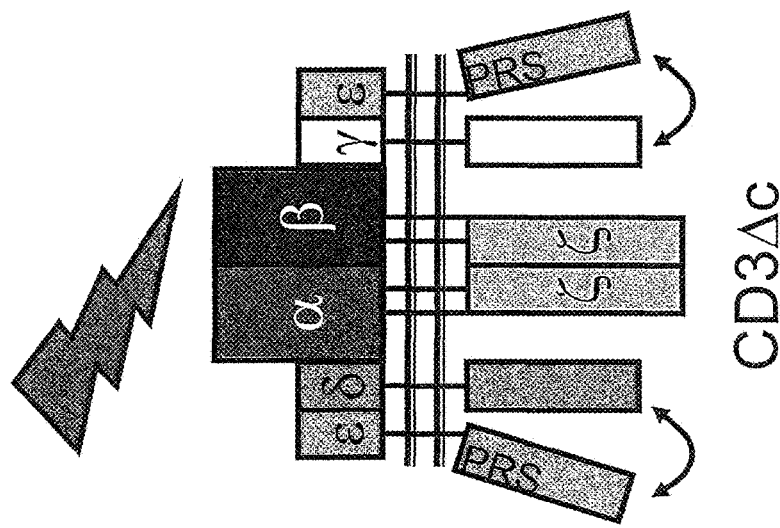

Figure 5

Requirements of reagent to achieve complementation of weak antigens :

- Binds specifically to T cells
- Induces CD3Δc
- Fails to stimulate T cell responses in the absence of TCR/Antigen binding
- Does not interfere with TCR/Antigen interaction Mono-7D6-Fab fulfills all these requirement

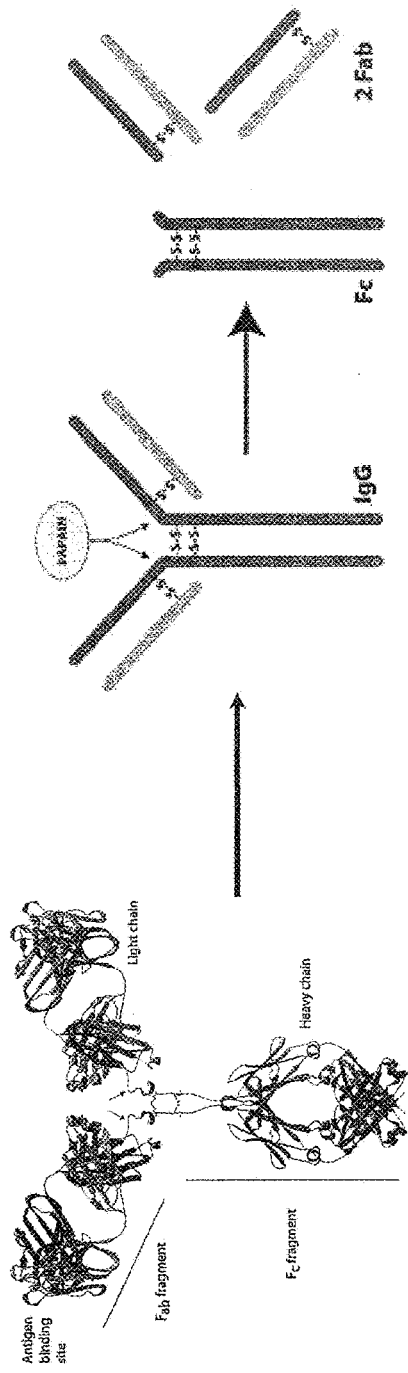
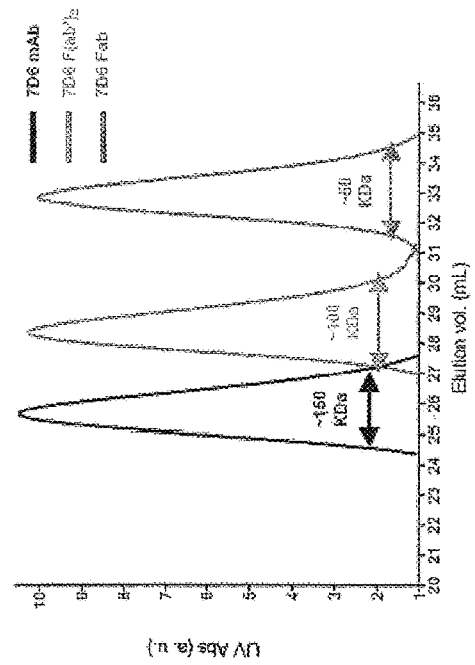
Figure 10

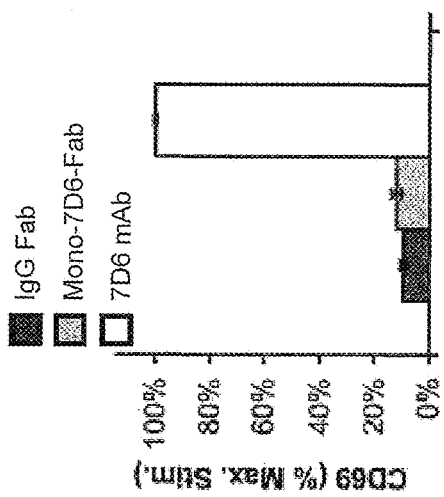
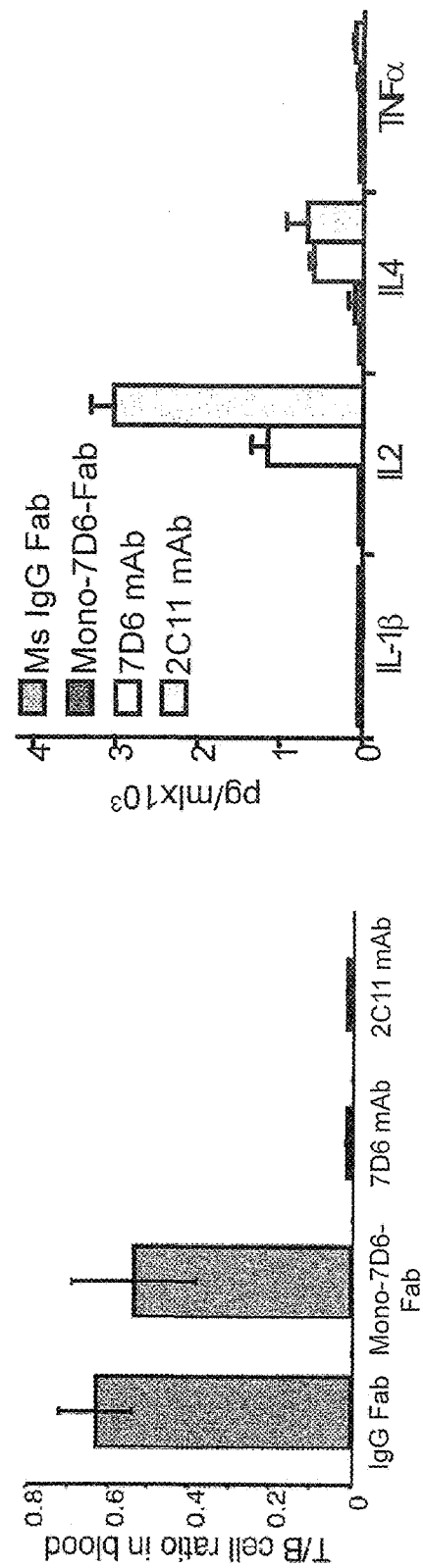
Figure 13

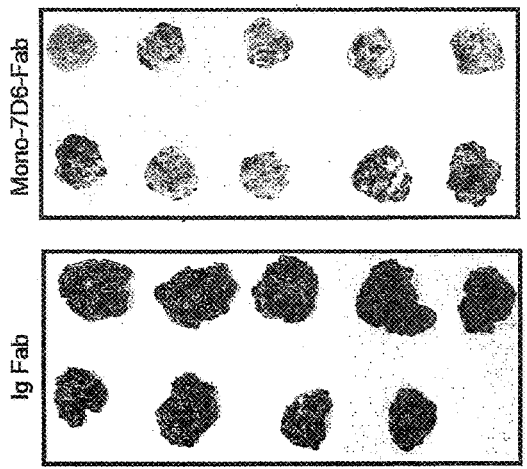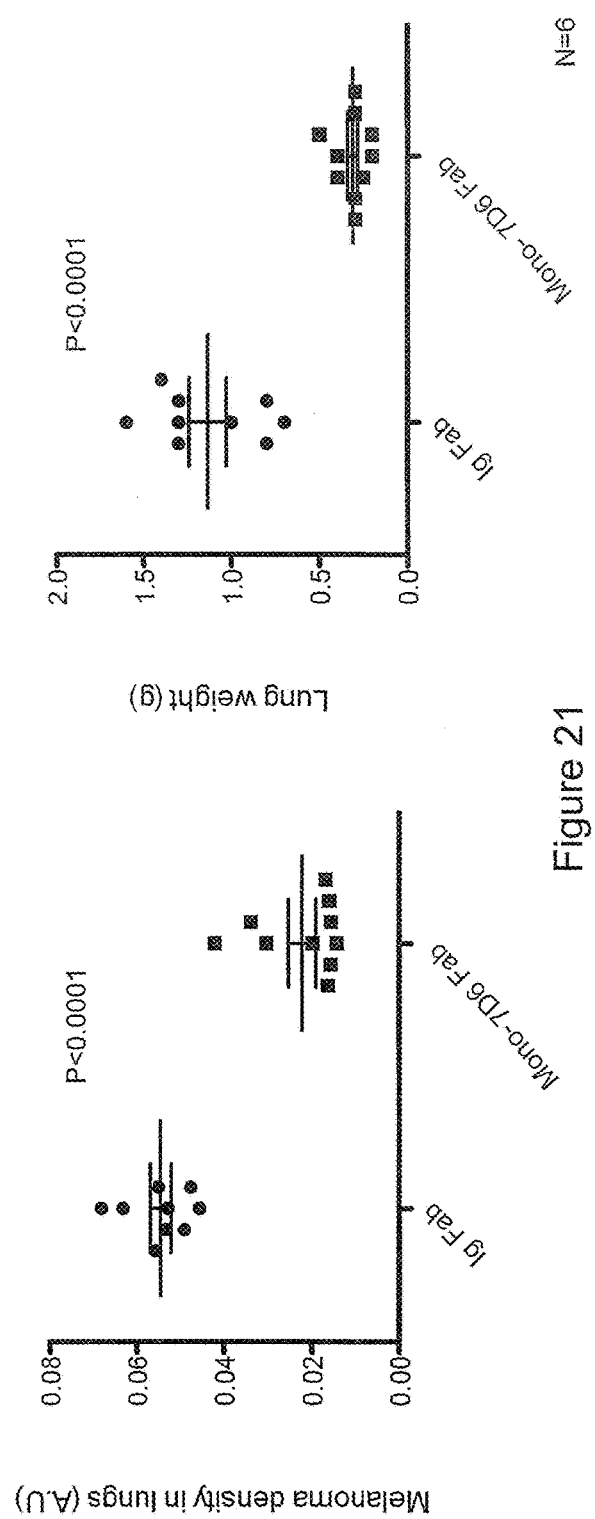
Figure 21. Injection of Mono-7D6-Fab results in decreased B16F10 metastatic melanoma tumor burden in B6 mice

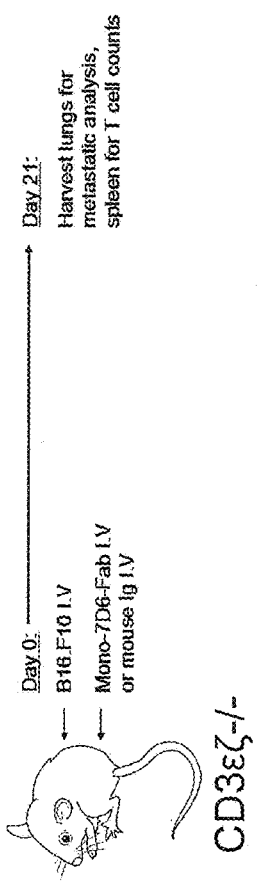
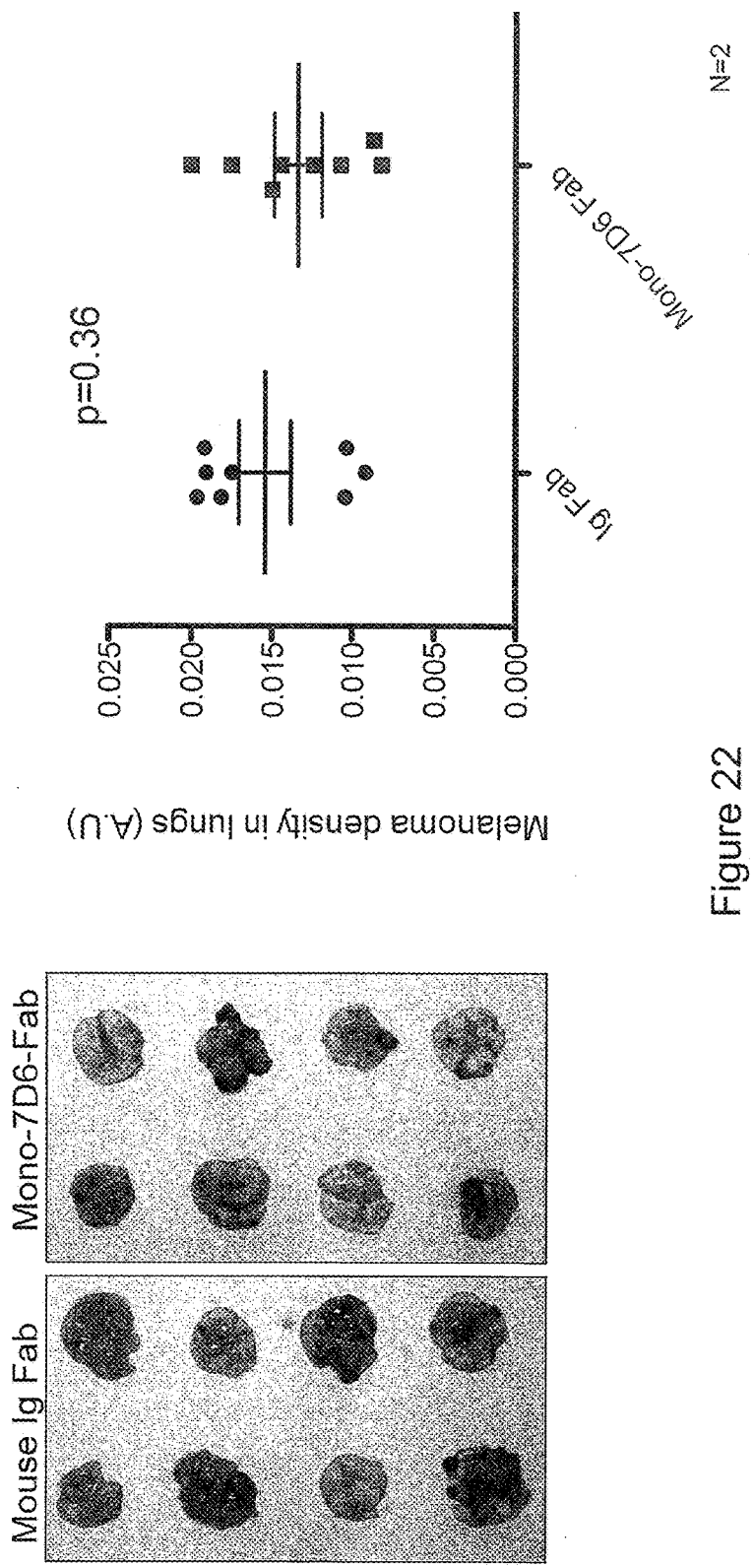
Figure 22

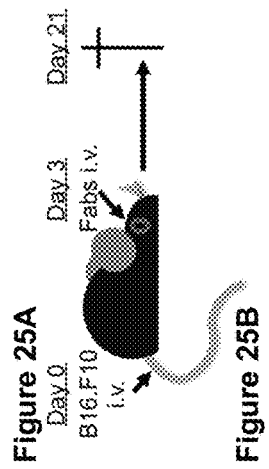
Figure 25A
Figure 25B
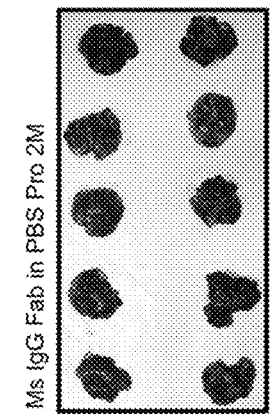
Figure 25C
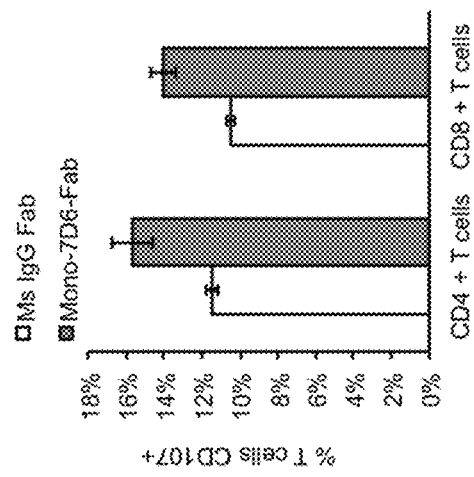
Figure 25D
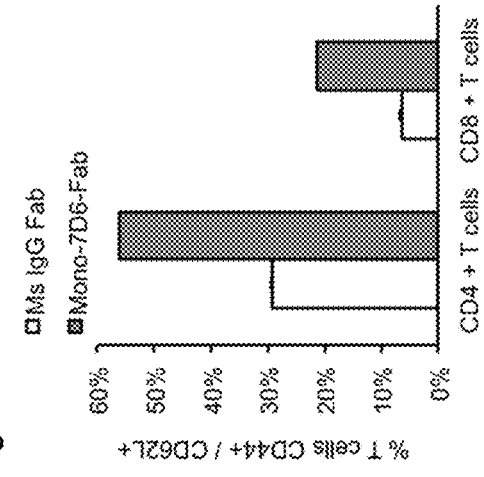
Figure 25E
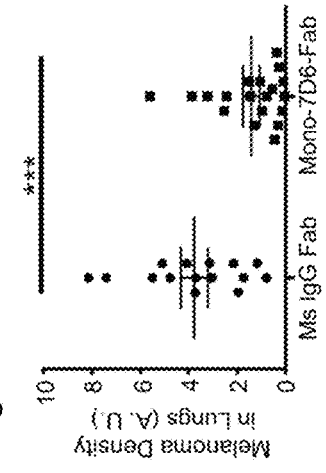

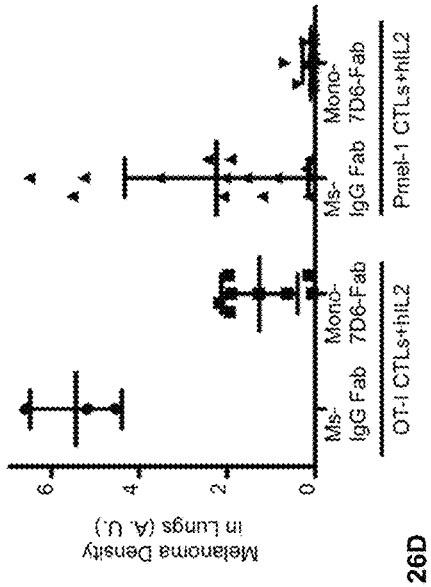
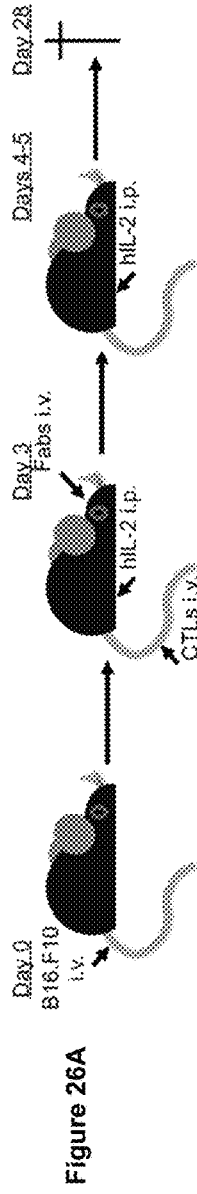
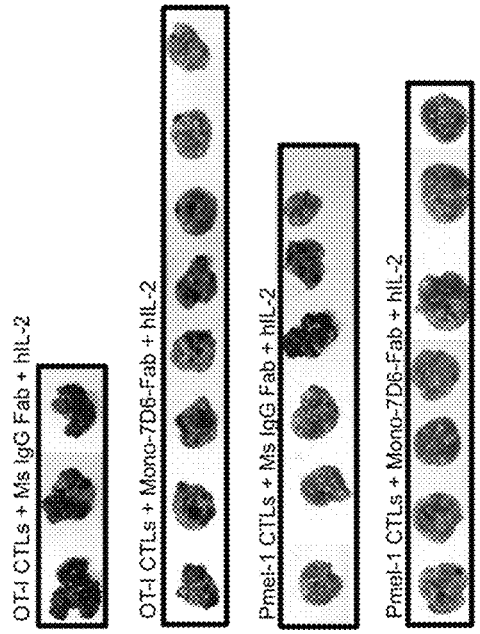
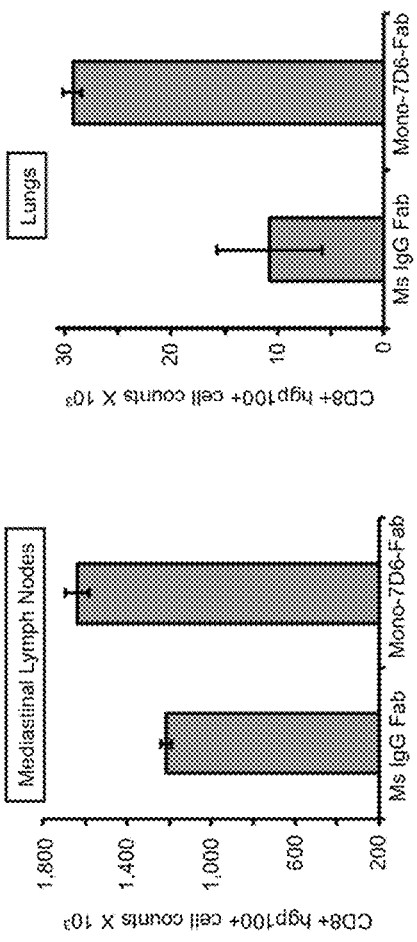
Figure 26A
Figure 26B
Figure 26C
Figure 26D

MONOVALENT ANTI-CD3 ADJUVANTS

CROSS-REFERENCE TO RELATED APPLICATIONS

This application is a continuation of U.S. application Ser. No. 15/426,745, filed Feb. 7, 2017, which is a continuation of U.S. application Ser. No. 14/571,601, filed Dec. 16, 2014, which claims the benefit of U.S. Provisional Application Ser. No. 61/918,545, filed Dec. 19, 2013. The disclosures of the prior applications are considered part of (and are incorporated by reference in) the disclosure of this application.

STATEMENT AS TO FEDERALLY SPONSORED RESEARCH

This invention was made with government support under AI097187 awarded by National Institutes of Health. The government has certain rights in the invention.

BACKGROUND

1. Technical Field

This document provides methods and materials related to using monovalent anti-CD3 antibodies (e.g., monovalent anti-CD3 Fab fragments) as adjuvants to increase the immune response produced against an antigen (e.g., a tumor associated antigen). For example, this document provides monovalent anti-CD3γε Fab fragments and vaccine compositions containing monovalent anti-CD3γε Fab fragments in combination with tumor associated antigens (e.g., tumor associated antigens having little or no immunogenicity in the absence of monovalent anti-CD3γε Fab fragments) as well as methods and materials for using monovalent anti-CD3γε Fab fragments to increase the immune response produced against an antigen (e.g., a tumor associated antigen) within a mammal (e.g., a human).

2. Background Information

Cancer is one of the leading causes of death in the world, responsible of about 13 percent of all human deaths. In spite of the significant advances achieved during recent decades, the efficiency of cancer treatments remains rather poor. Unfortunately, main treatments like radio- and chemotherapy do not specifically target cancer cells, damaging healthy tissues as well. As a result, these kinds of cancer therapies themselves cause significant morbidity and mortality. On the other hand, these treatments frequently fail to eradicate cancer cells efficiently, leading to cancer recurrence.

Immunotherapy is an attractive alternative to treat cancer. The immune system has the capacity to identify cancer cells specifically, sparing healthy tissue from its attack. The main goal when stimulating the immune system against a tumor using vaccination strategies is to achieve an efficient anti-tumor T cell response that not only is specific for the cancer but also develops memory to control potential recurrence. T cell activation depends on T cells receiving three signals. Signal one consists of the recognition by the T cell receptor (TCR) of a foreign antigen in the shape of a peptide/MHC on the surface of professional antigen presenting cells (APCs). Co-stimulatory molecules on the APCs and their corresponding receptors in T cells provide signal two. Signal three is provided by soluble cytokines present in the T cell milieu.

Tumor associated antigens (TAA) come from mutated self-proteins, over/aberrantly expressed self-proteins, or unique foreign proteins from oncoviruses that are expressed by tumor cells. When mutated or from viral origin, tumor proteins might generate unique TAAs that can stimulate the TCR efficiently. However, in most cases, TAAs are closely related with self-proteins and are not very efficient in providing signal one. Some immunotherapies focus on the development of anti-tumor vaccines that incorporate the use of adjuvants that function to increase the efficiency of signals two and three such as toll like receptor ligands (e.g., CpG and MLP), cytokines, (e.g., IL-2, IL-12, and IFNα/β), and chemokines (e.g., GM-CSF).

The option to improve the poorly immunogenic nature of most TAAs is reduced to a strategy of vaccinating mammals with altered peptide ligands (APLs). In an attempt to compensate for the weakness of signal one provided by TAAs, the sequence of the natural tumor peptide is modified to increase its affinity for the MHC and/or the TCR, with the expectation that the immunogenicity of the resulting APL will be higher than the natural TAA. This strategy, however, can be limited by the fact that once the natural tumor peptide is modified, (i) the TCRs stimulated by the APLs may not be specific to the natural TAAs from the tumor, (ii) the T cells may become anergized by the natural TAAs from the tumor, and/or (iii) the TCRs may be specific for other tissues, thereby displaying undesired side effects.

SUMMARY

This document provides methods and materials related to using monovalent anti-CD3 antibodies (e.g., monovalent anti-CD3 Fab fragments) as adjuvants to increase the immune response produced against an antigen (e.g., a tumor associated antigen). For example, this document provides monovalent anti-CD3γε Fab fragments as well as vaccine compositions containing monovalent anti-CD3γε Fab fragments in combination with tumor associated antigens. In some cases, the tumor associated antigen can be an antigen having little or no immunogenicity in the absence of monovalent anti-CD3γε Fab fragments. This document also provides methods and materials for using monovalent anti-CD3γε Fab fragments to increase the immune response produced against an antigen (e.g., a tumor associated antigen) within a mammal (e.g., a human).

As described herein, monovalent anti-CD3γε Fab fragments can be used to increase the immune response produced against an antigen (e.g., a tumor associated antigen). For example, monovalent anti-CD3γε Fab fragments provided herein can be used to increase the immunogenicity of natural TAAs without having to change their peptide sequences. In some cases, a monovalent anti-CD3γε Fab fragment provided herein can be used to increase the immunogenicity of a natural TAA, an APL, a mixture of different TAAs, a mixture of different APLs, or a mixture of TAAs and APLs. In some cases, a monovalent anti-CD3γε Fab fragment provided herein can be used to increase the immunogenicity of tumor associated antigens in the form of a tumor cell lysate. For example, monovalent anti-CD3γε Fab fragments provided herein can be combined with a tumor cell lysate to produce a mixture that is more immunogenic than the tumor cell lysate alone. In some cases, the monovalent anti-CD3γε Fab fragments provided herein can be used in combination with tumor associated antigens and other particular adjuvants designed to increase signal two and/or signal three of T cell activation.

In general, one aspect of this document features a method for increasing an immune response against an antigen. The method comprises, or consists essentially of, administering a composition comprising a monovalent anti-CD3γε antibody preparation and the antigen or nucleic acid that expresses the antigen to a mammal, wherein the monovalent anti-CD3γε antibody preparation comprises Fab fragments of an anti-CD3γε antibody, and wherein the mammal produces an immune response against the antigen that is increased as compared to an immune response produced against the antigen when the antigen or the nucleic acid is administered to a comparable mammal in the absence of the monovalent anti-CD3γε antibody preparation. The mammal can be a human, and the Fab fragments can be Fab fragments of an anti-human CD3γε antibody. The Fab fragments can be Fab fragments of a humanized anti-human CD3γε antibody. The Fab fragments can be Fab fragments of a fully human anti-human CD3γε antibody. The antigen can be a tumor associated antigen. The tumor associated antigen can be a polypeptide. The antigen can be within an extract from a whole tumor cell lysate. The method can comprise administering the antigen to the mammal. The method can comprise administering the nucleic acid to the mammal.

In another aspect, this document features a method for increasing an immune response against a cancer antigen. The method comprises, or consists essentially of, administering a composition comprising a monovalent anti-CD3γε antibody preparation to a mammal having cancer cells, wherein the monovalent anti-CD3γε antibody preparation comprises Fab fragments of an anti-CD3γε antibody, and wherein the mammal produces an immune response against the antigen that is increased as compared to an immune response produced against the cancer antigen in a comparable mammal not administered the monovalent anti-CD3γε antibody preparation. The mammal can be a human, and the Fab fragments can be Fab fragments of an anti-human CD3γε antibody. The Fab fragments can be Fab fragments of a humanized anti-human CD3γε antibody. The Fab fragments can be Fab fragments of a fully human anti-human CD3γε antibody. The antigen can be a tumor associated antigen. The tumor associated antigen can be a polypeptide. The antigen can be within an extract from a whole tumor cell lysate. The method can comprise administering the antigen to the mammal. The method can comprise administering nucleic acid encoding the antigen to the mammal. The method can comprise administering tumor specific cytotoxic T lymphocytes to the mammal. The method can comprise administering an IL-2 polypeptide to the mammal.

In another aspect, this document features a method for increasing an immune response against an antigen. The method comprises, or consists essentially of, administering a composition comprising a monovalent anti-CD3γε antibody preparation and tumor specific cytotoxic T lymphocytes, wherein the monovalent anti-CD3γε antibody preparation comprises Fab fragments of an anti-CD3γε antibody, and wherein the mammal produces an immune response against the antigen that is increased as compared to an immune response produced against the antigen when the tumor specific cytotoxic T lymphocytes are administered to a comparable mammal in the absence of the monovalent anti-CD3γε antibody preparation. The mammal can be a human, and the Fab fragments can be Fab fragments of an anti-human CD3γε antibody. The Fab fragments can be Fab fragments of a humanized anti-human CD3γε antibody. The Fab fragments can be Fab fragments of a fully human anti-human CD3γε antibody. The antigen can be a tumor associated antigen. The tumor associated antigen can be a polypeptide. The method can comprise administering the antigen to the mammal. The method can comprise administering a nucleic acid encoding the antigen to the mammal. The method can comprise administering an IL-2 polypeptide to the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4 contains a diagram (left) of how an APA 1/1 antibody to the cytoplasmic tail of CD3ε blocks the pull down of Nck SH3.1, and a diagram (right) of how an 2C11 antibody to an extracellular domain of CD3ε promotes the open conformation allowing detection by the pull down of Nck SH3.1.

FIG. 5 is a diagram of a T cell receptor/CD3 complex in an open conformation (CD3Δc) along with a list of properties.

FIG. 9 contains a diagram of a monovalent anti-CD3γε Fab fragment (e.g., Mono-7D6-Fab) bound to the extracellular domains of CD3γε in a manner that triggers the open CD3Δc conformation.

FIG. 10 contains a schematic diagram and graph showing the digestion of the 7D6 monoclonal antibody into Fab and Fc fragments.

FIG. 13 contains graphs demonstrating that Mono-7D6-Fab alone does not stimulate T cells.

FIG. 21 contains a set of photographs of lung tissue from mice injected with B16.F10 tumor cells on day 0 and treated intravenously with mouse Ig Fab (10 μg/mouse on day 0) or Mono-7D6-Fab (10 μg/mouse on day 0). On day 21, the lungs were extracted and evaluated for the presence of metastatic melanoma tumor burden. Less melanoma burden was observed in mice treated with Mono-7D6-Fab. The two dot-plots present two different means of objective melanoma quantification in the lungs of each group of mice. On the left plot, melanoma density was quantified using software that detects dark melanoma tissue in the lungs. On the right plot, lung weight was plotted to reflect the amount of melanoma burden. Both plots reveal a statistical difference in the melanoma burden between the mouse IgG Fab treated mice (higher burden) and the Mono-7D6-Fab treated mice (lower burden).

FIG. 22 contains photographs of lung tissue from mice lacking T cells (CD3εζ$^{-/-}$mice) injected with B16.F10 tumor cells on day 0 and treated intravenously with mouse Ig Fab; (10 μg/mouse on day 0) or Mono-7D6-Fab (10 μg/mouse on day 0). On day 21, the lungs were extracted and evaluated for the presence of metastatic melanoma tumor burden. Similar tumor burden was observed in both treatment groups, demonstrating that T cells are required for the response observed in FIG. 21. On the left, there is an objective quantification of tumor burden in lung of mice of each group treatment using a dot plot that depicts melanoma density as specified in FIG. 21. There is not a statistical difference in the melanoma burden between the mouse IgG Fab treated mice and the Mono-7D6-Fab treated mice.

FIGS. 25A-E. Mono-7D6-Fab promotes therapeutic anti-tumor T cell responses in the B16F10/B6 lung metastatic melanoma model when administered three days after tumor injection. FIG. 25A is a schematic summary of the experimental procedure. FIG. 25B contains photographs of the lungs that were evaluated for the presence of metastatic melanoma tumor burden. FIG. 25C is a graph plotting melanoma density for mice treated with the indicated Fab (t test, ***p<0.0001). FIG. 25D is a graph plotting the percent of T cells positive for CD107a. FIG. 25E is a graph plotting the percent of T cells positive for CD44 and CD62L.

FIGS. 26A-D. Anti-melanoma effect when Mono-7D6-Fab therapy is combined with adoptive transfer of melanoma specific cytotoxic lymphocytes. FIG. 26A is a schematic summary of the experimental procedure. FIG. 26B contains photographs of the lungs that were evaluated for the presence of metastatic melanoma tumor burden. FIG. 26C is a graph plotting melanoma density for mice treated with the indicated Fab and CTLs. FIG. 26D is a graph plotting the number of CD8 T cells from mediastinal lymph node or lung that stained with the Kd-tetramer gp100 to identify cells specific for the melanoma antigen gp100.

DETAILED DESCRIPTION

Figure 1:
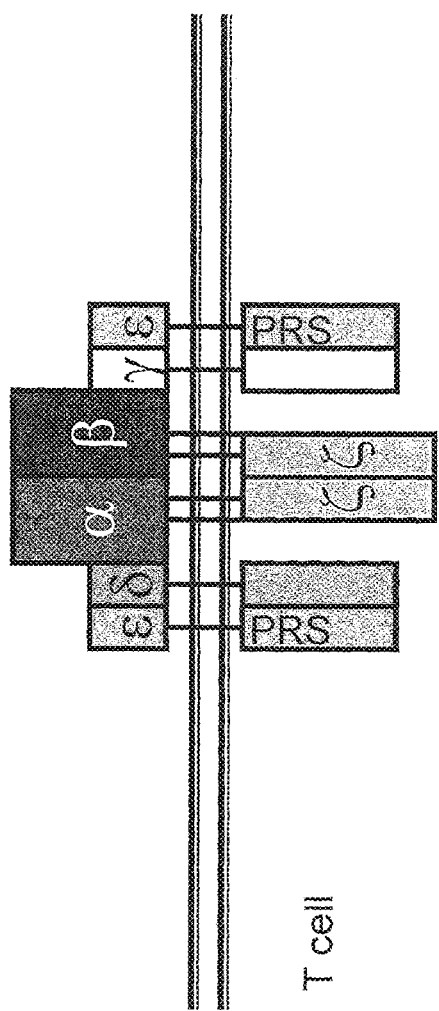
FIG. 1 is a diagram of a T cell receptor/CD3 complex of a T cell that is in the closed conformation.

This document provides methods and materials related to monovalent anti-CD3γε antibodies (e.g., monovalent anti-CD3 Fab fragments). For example, this document provides monovalent anti-CD3γε antibody preparations, methods for making monovalent anti-CD3γε antibody preparations, and methods for using monovalent anti-CD3γε antibody preparations as adjuvants to increase the immune response produced against an antigen (e.g., a tumor associated antigen). For example, this document provides monovalent anti-CD3γε Fab fragments as well as vaccine compositions containing monovalent anti-CD3γε Fab fragments in combination with tumor associated antigens. In some cases, the tumor associated antigen can be an antigen having little or no immunogenicity in the absence of monovalent anti-CD3γε Fab fragments. This document also provides methods and materials for using monovalent anti-CD3γε Fab fragments to increase the immune response produced against an antigen (e.g., a tumor associated antigen) within a mammal (e.g., a human).

In some cases, a monovalent anti-CD3γε antibody preparation provided herein can bind to a CD3γε dimer with little or no detectable binding to a CD3ε polypeptide not in the form of a CD3γε dimer and with little or no detectable binding to a CD3γ polypeptide not in the form of a CD3γε dimer. For example, a monovalent anti-CD3γε antibody preparation provided herein can bind to a human CD3γε dimer with little or no detectable binding to a human CD3ε polypeptide not in the form of a CD3γε dimer and with little or no detectable binding to a human CD3γ polypeptide not in the form of a CD3γε dimer. An example of an antibody having the ability to bind to a CD3γε dimer with little or no detectable binding to a CD3ε polypeptide not in the form of a CD3γε dimer and with little or no detectable binding to a CD3γ polypeptide not in the form of a CD3γε dimer includes, without limitation, the 7D6 antibody described elsewhere (Van Snick et al., *Eu. J. Immunol.*, 21:1703-1709 (1991)). Fab fragments from such an antibody can be used to obtain monovalent anti-CD3γε antibodies (e.g., monovalent anti-CD3γε Fab fragments).

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

The antibodies provided herein that can be used to make a monovalent anti-CD3γε Fab fragments provided herein can be any antibody (e.g., a monoclonal antibody) having binding affinity (e.g., specific binding affinity) for a CD3γε dimer with little or no detectable binding to a CD3ε polypeptide not in the form of a CD3γε dimer or a CD3γ polypeptide not in the form of a CD3γε dimer. For example, a monovalent anti-CD3γε antibody preparation can be a preparation of Fab fragments having the ability to bind to a CD3γε dimer with little or no detectable binding to a CD3ε polypeptide not in the form of a CD3γε dimer and with little or no detectable binding to a CD3γ polypeptide not in the form of a CD3γε dimer.

Any appropriate method can be used to produce Fab fragments from intact antibodies. For example, standard papain digestion methods can be used to make an Fab antibody preparation. In some cases, a monovalent anti-CD3γε antibody preparation provided herein can be a preparation of Fab fragments of humanized or fully-human anti-human CD3γε dimer antibodies. In some cases, a monovalent anti-CD3γε antibody preparation provided herein (e.g., a monovalent anti-CD3γε antibody preparation containing Fab fragments of a humanized anti-CD3γε antibody) can have the ability to increase the immune response produced against an antigen (e.g., a tumor associated antigen).

Antibodies provided herein can be prepared using any appropriate method. For example, a sample containing a CD3γε dimer (e.g., a human CD3γε dimer or a chimeric mouse/human CD3γε dimer) can be used as an immunogen to elicit an immune response in an animal such that specific antibodies are produced. The immunogen used to immunize an animal can be chemically synthesized or derived from translated cDNA. In some cases, cells (e.g., mouse T cells) transfected to express a CD3γε dimer (e.g., a human CD3γε dimer or a chimeric mouse/human CD3γε dimer) can be used as an immunogen. In some cases, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan et al., Unit 9, Current Protocols in Immunology, Wiley Interscience, 1994).

The preparation of monoclonal antibodies also is well-known to those skilled in the art. See, e.g., Kohler & Milstein, Nature 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, methods of in vitro and in vivo multiplication of monoclonal antibodies are well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., *Int. J. Cancer,* 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., *Proc. Nat'l. Acad. Sci. USA* 86:3833 (1989). Techniques for producing humanized monoclonal antibodies are described, for example, by Jones et al., *Nature* 321:522 (1986); Riechmann et al., *Nature* 332:323 (1988); Verhoeyen et al., *Science* 239:1534 (1988); Carter et al., *Proc. Nat'l. Acad. Sci. USA* 89:4285 (1992); and Sandhu, *Crit. Rev. Biotech.* 12:437 (1992); Singer et al., *J. Immunol.* 150:2844 (1993). In some cases, humanization such as super humanization can be used as described elsewhere (Hwang et al., *Methods,* 36:35-42 (2005)). In some cases, SDR grafting (Kashmiri et al., *Methods,* 36:25-34 (2005)), human string content optimization (Lazar et al., *Mol. Immunol.,* 44:1986-1998 (2007)), framework shuffling (Dall'Acqua et al., *Methods,* 36:43-60 (2005); and Damschroder et al., *Mol. Immunol.,* 44:3049-3060 (2007)), and phage display approaches (Rosok et al., *J. Biol. Chem.,* 271:22611-22618 (1996); Radar et al., *Proc. Natl Acad. Sci. USA,* 95:8910-8915 (1998); and Huse et al., *Science,* 246:1275-1281 (1989)) can be used to obtain anti-CD3γε antibody preparations. In some cases, fully human antibodies can be generated from recombinant human antibody library screening techniques as described elsewhere (Griffiths et al., *EMBO J.,* 13:3245-3260 (1994); and Knappik et al., *J. Mol. Biol.,* 296:57-86 (2000)).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., *Ann. Rev. Immunol.* 12: 433 (1994). Cloning and expression vectors that are useful for producing a human immunoglobulin phage library can be obtained, for example, from STRATAGENE Cloning Systems (La Jolla, Calif.).

In addition, antibodies provided herein can be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al. (*Nature Genet.,* 7:13 (1994)), Lonberg et al. (*Nature,* 368:856 (1994)), and Taylor et al. (*Int. Immunol.,* 6:579 (1994)).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, Fab fragments can be produced by enzymatic cleavage of antibodies with papain. In some cases, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

As described herein, the monovalent anti-CD3γε Fab fragments provided herein can be used to increase the immune response produced against an antigen. Examples of such antigens include, without limitation, germ cell-cancer associated tumor antigens, tumor antigens derived from genetic mutations and atypical gene products, tumor differentiation antigens, and tumor polypeptide ligands. Antigens (e.g., tumor associated antigens) can be administered as, for example, polypeptides (e.g., short or truncated polypeptides or full length polypeptides), DNA encoding such polypeptides, viral particles designed to express such polypeptides, extracts from whole tumor cell lysates, or dendritic cells loaded with such polypeptides or tumor cell lysates. Examples of tumor polypeptide ligands include, without limitation, altered peptide ligands (APLs), xenogeneic tumor peptides, and heteroclitic tumor peptides.

In some cases, a monovalent anti-CD3γε Fab fragment provided herein can be combined with one or more antigens to produce a vaccine composition. For example, a monovalent anti-human CD3γε Fab fragment preparation can be combined with a tumor associated antigen such as whole tumor protein, whole tumor cell lysate, or an altered, xenogeneic, orheteroclitic tumor peptides derived from a whole tumor protein to produce a vaccine composition capable of producing an immune response against tumor cells that is increased in comparison to a comparable vaccine composition lacking monovalent anti-human CD3γε Fab fragments.

In some cases, a monovalent anti-CD3γε Fab fragment provided herein can be used to increase the immunogenicity of tumor associated antigens provided in the form of a tumor cell lysate. For example, monovalent anti-CD3γε Fab fragments provided herein can be combined with a tumor cell lysate to produce a mixture or vaccine composition that is more immunogenic than the tumor cell lysate alone.

In some cases, a vaccine composition can include additional components such as adjuvants designed to increase signal two and/or signal three of T cell activation. Examples of adjuvants designed to increase signal two of T cell activation include, without limitation, Freund's adjuvants and Toll like receptor ligands (like LPS, CpG, and PolyI:C). Examples of adjuvants designed to increase signal three of T cell activation include, without limitation, cytokines (IL-2, IL-12, IFNα, or IFNβ), and chemokines (GM-CFS).

In some cases, a human monovalent CD3εγ-Fab preparation specific for human T cells can be used as an adjuvant to increase the immunogenicity of natural TAAs. Such a human reagent can allow the development of tumor vaccines using natural TAA avoiding the problems related with anti-tumor vaccines: limited repertoire of TAAs immunogenic enough to be considered for the development the vaccine, very intricate design of APLs derived from the analogue natural TAAs to achieve higher affinity for MHC and/or TCR molecules, high risk of stimulating a T cell repertoire not specific for the natural TAAs when using such APLs, together with high risk of promoting adverse effects of stimulated T cell repertoire by the vaccine, and the need to personalize the selection of APLs used to immunize. Additionally, using a human monovalent CD3εγ-Fab preparation to boost natural TAA immunogenicity can be compatibility with: (i) vaccines using single TAAs, TAAs mixtures or tumor lysates as a source of tumor antigenic specificity; or (ii) any existing or new adjuvants designed to increase signal two and/or three to stimulate T cells.

The invention will be further described in the following examples, which do not limit the scope of the invention described in the claims.

EXAMPLES

Figure 8:
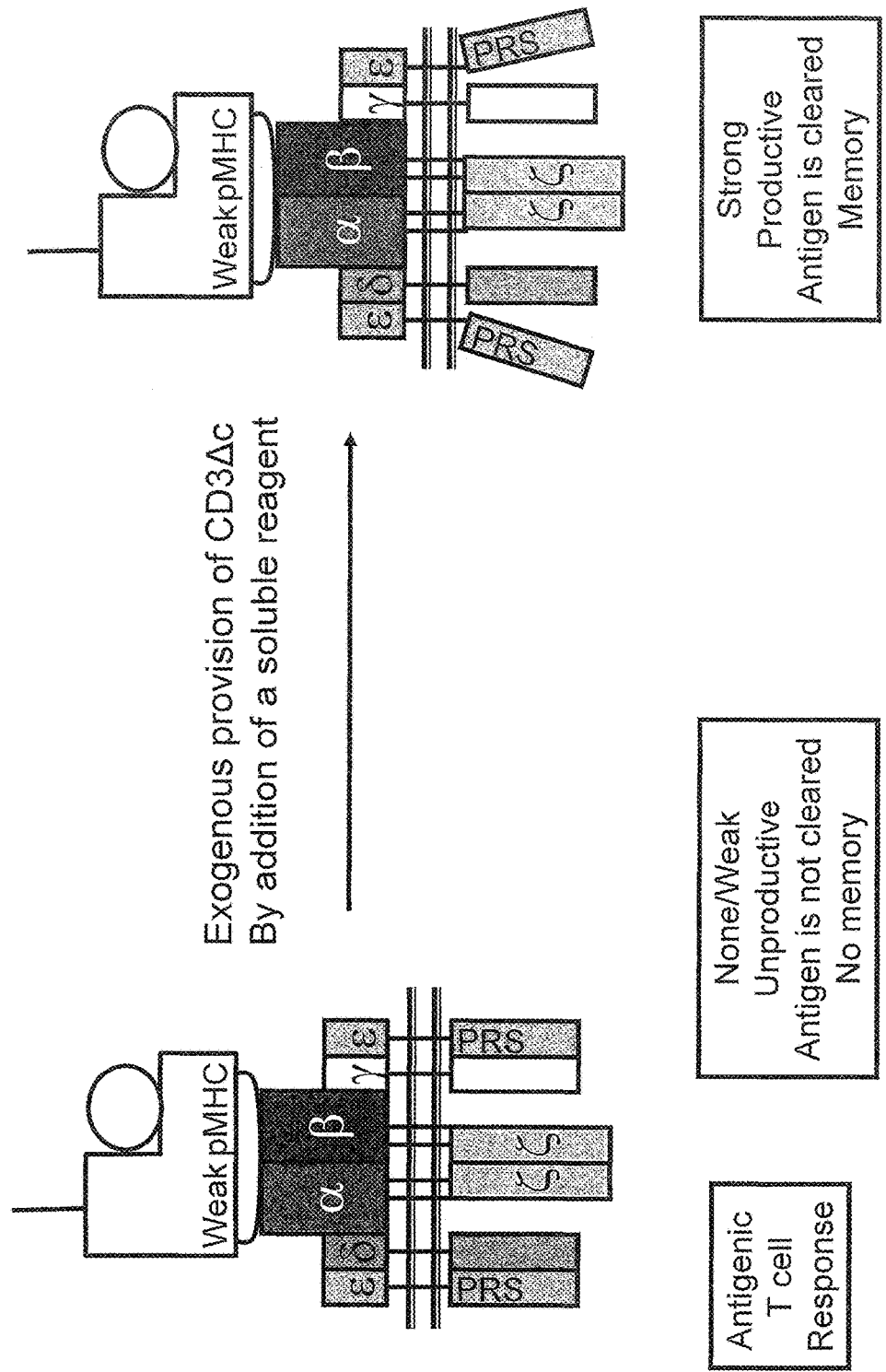
FIG. 8 contains a diagram representing how a soluble agent can produce the open CD3Δc conformation even though a poorly immunogenic or non-immunogenic antigen in combination with an MHC molecule is engaging the T cell receptor/CD3 complex.

Example 1—Using Monovalent Anti-CD3γε Dimer Fab Fragments as Adjuvants to Increase Immunogenicity Mono-7D6-Fab specific for mouse T cells was capable of increasing the immunogenicity of antigens that are weak and poorly immunogenic (FIGS. 8-9). Mono-7D6-Fab is a monovalent Fab fragment specific for the CD3εγ dimer of the CD3 complex (FIGS. 1, 9, and 10). The following was performed to confirm the ability of Mono-7D6-Fab to increase the immunogenicity of antigens in the context of cancer disease using a mouse model of lung metastatic melanoma (FIGS. 20-24).

Figure 2:
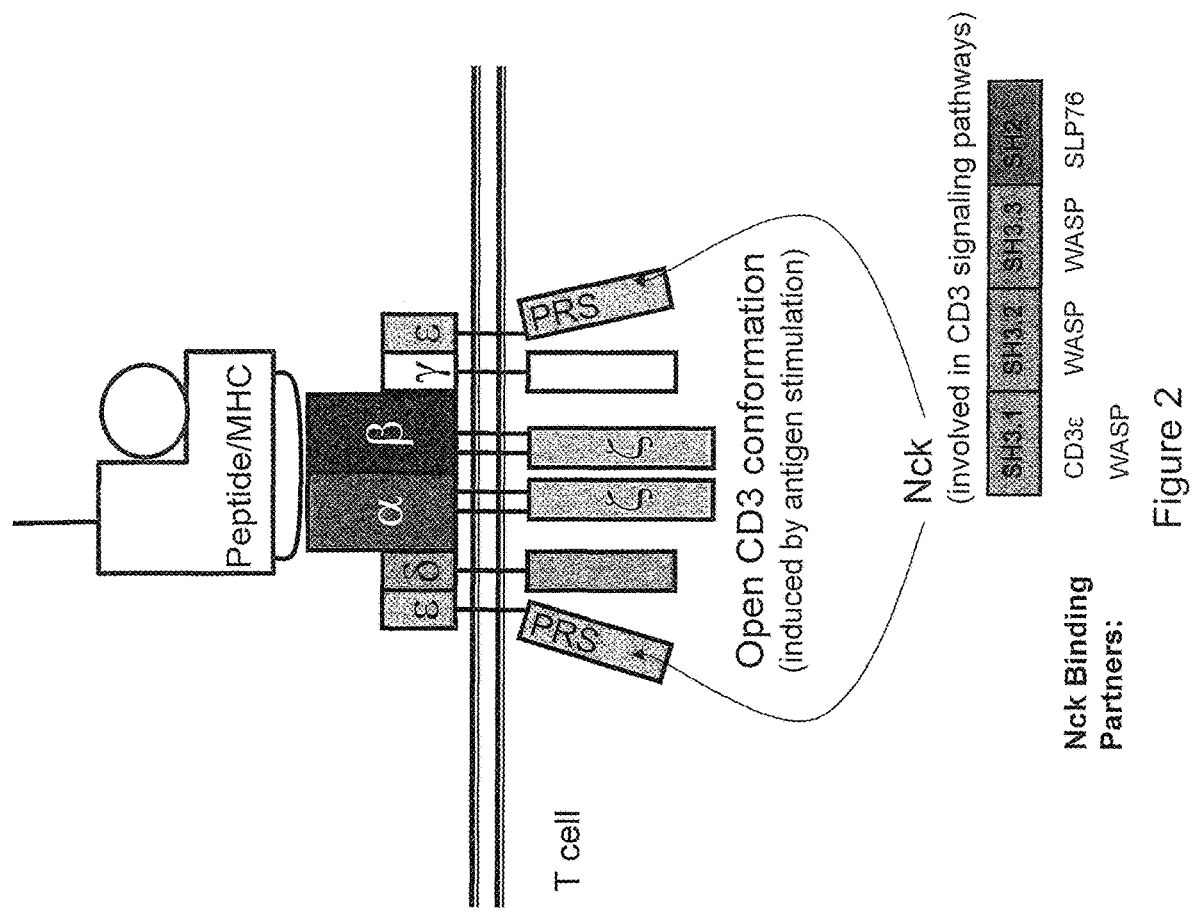
FIG. 2 is a diagram of a T cell receptor/CD3 complex of a T cell that is in an open conformation (CD3Δc), which can be induced by the binding of a peptide/MHC complex.
Figure 3:
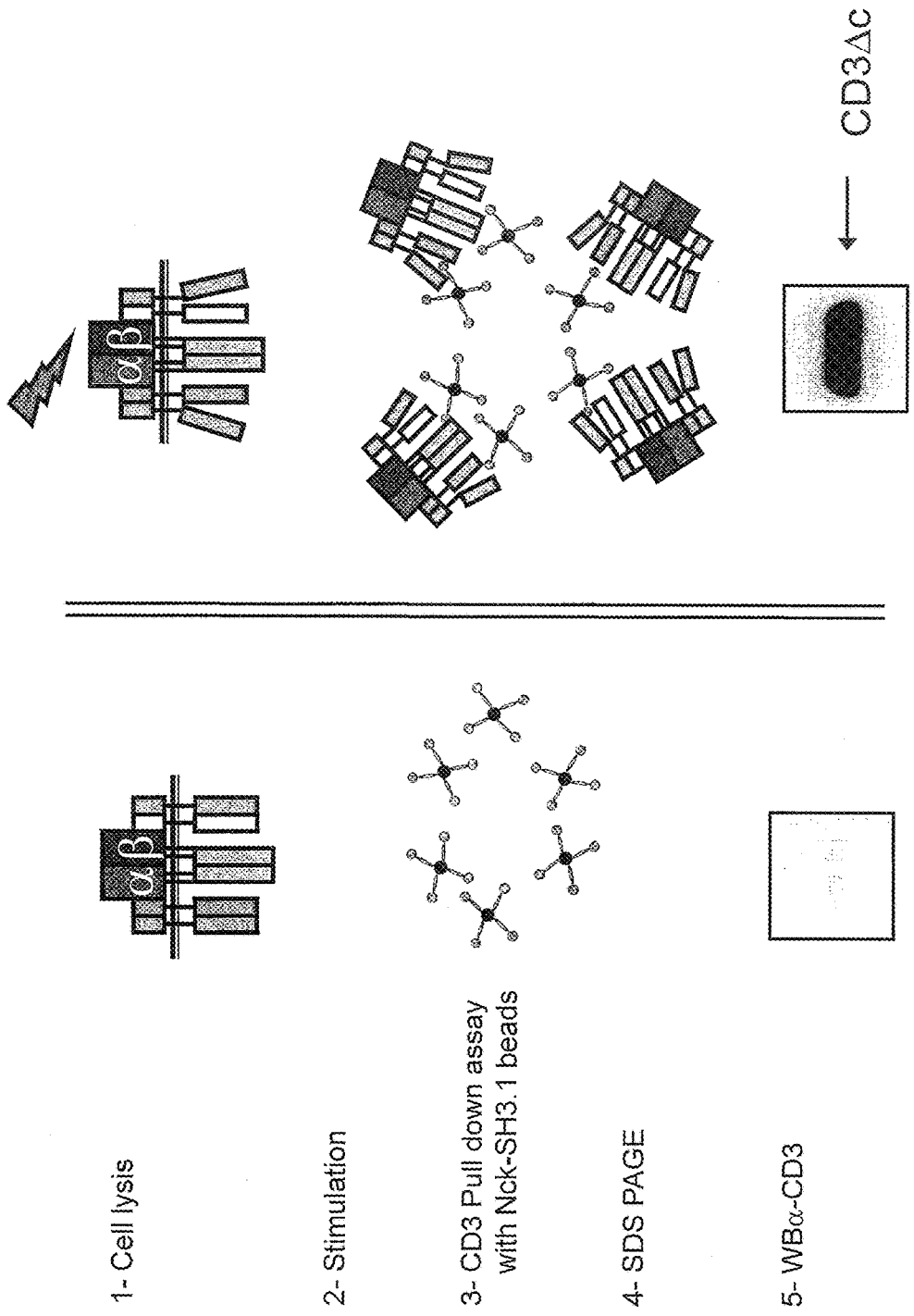
FIG. 3 is a diagram of a CD3 pull down (CD3-PB) assay using Nck-SH3.1 beads and a western blot with anti-CD3ζ antibodies.
Figure 6:
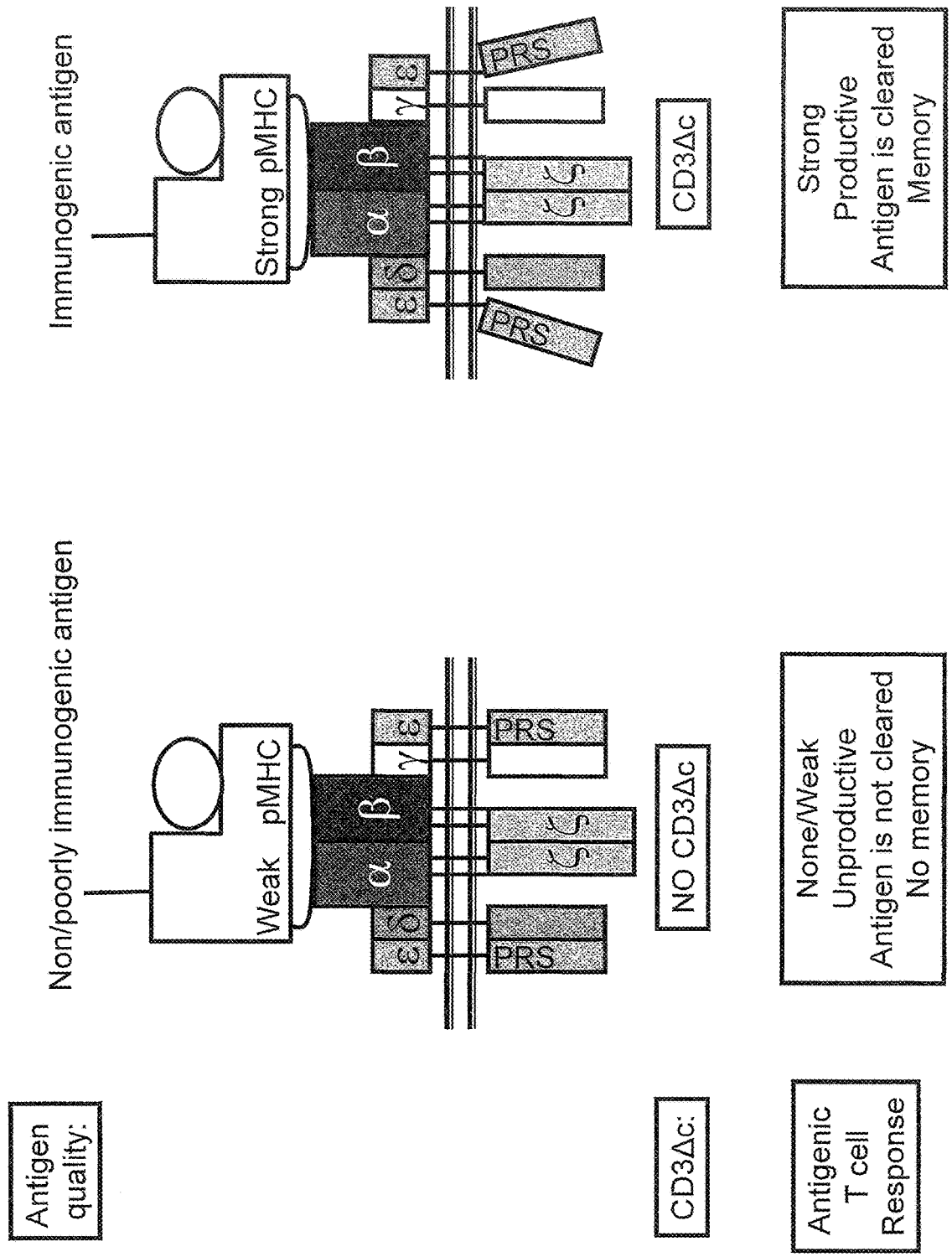
FIG. 6 contains a diagram (left) of how poorly immunogenic or non-immunogenic antigens in combination with MHC molecules do not result in the CD3Δc conformation, and a diagram (right) of how immunogenic antigens in combination with MHC molecules do result in the CD3Δc conformation.
Figure 7:
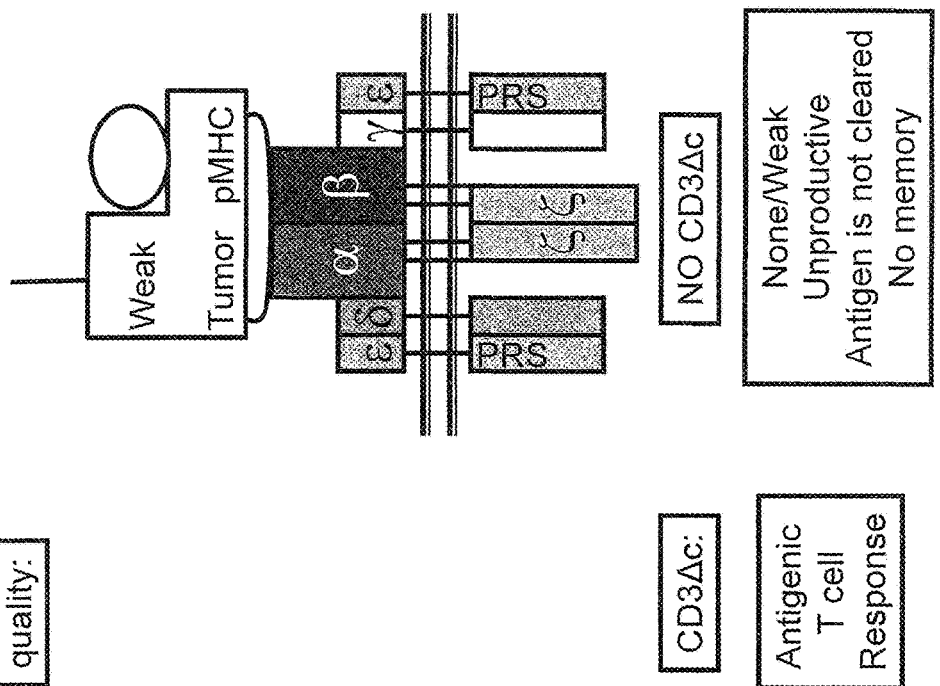
FIG. 7 contains a diagram of how most TAA are poorly immunogenic or non-immunogenic antigens that when in combination with MHC molecules do not result in the CD3Δc conformation.
Figure 11:
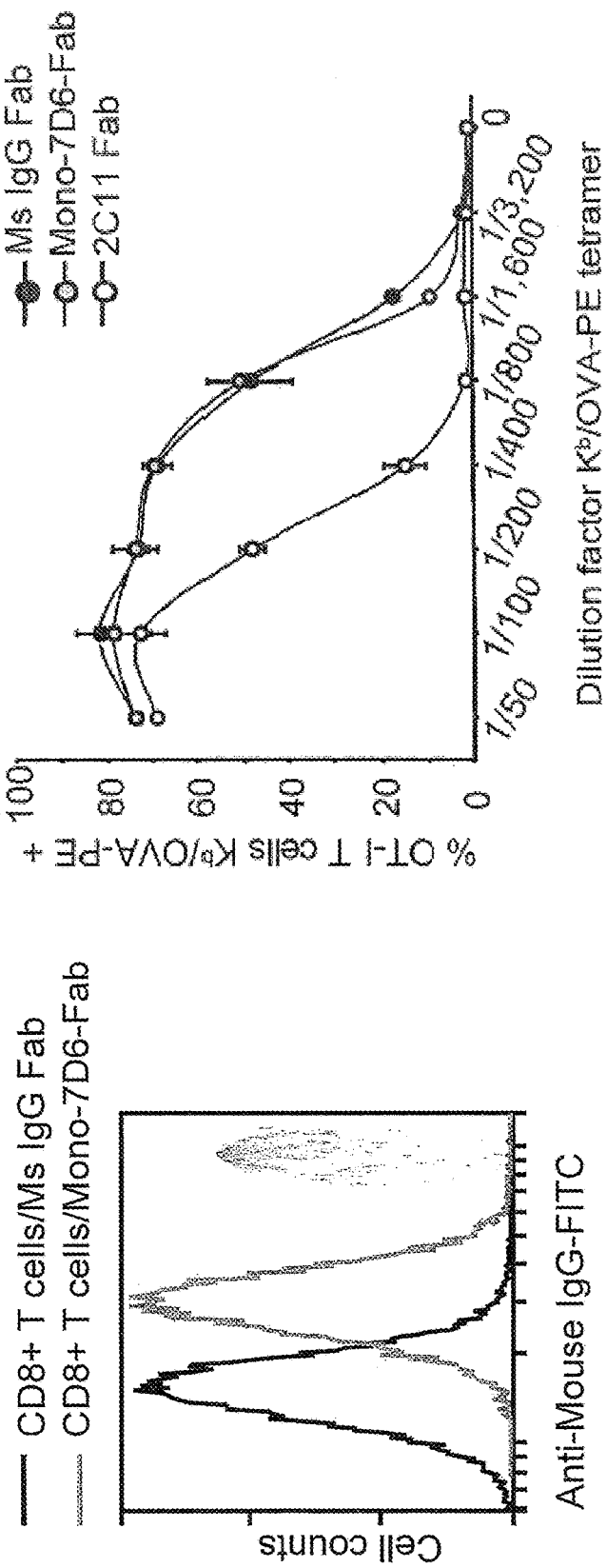
FIG. 11 contains graphs demonstrating that Mono-7D6-Fab binds to the T cell receptor and does not block the binding of peptide/MHC complexes (pMHC7) to T cell receptors. Ms IgG Fab is a non-specific Fab control for Mono-7D6-Fab.
Figure 12:
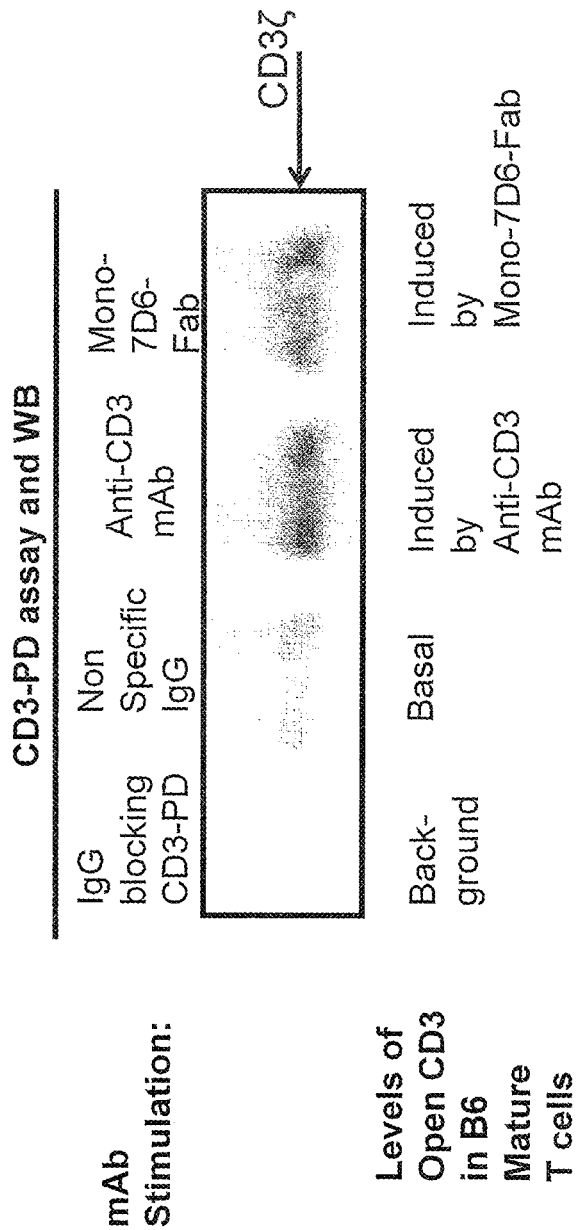
FIG. 12 is a western blot demonstrating that Mono-7D6-Fab induces the open CD3Δc conformation in mature T cells obtained from mice.
Figure 14:
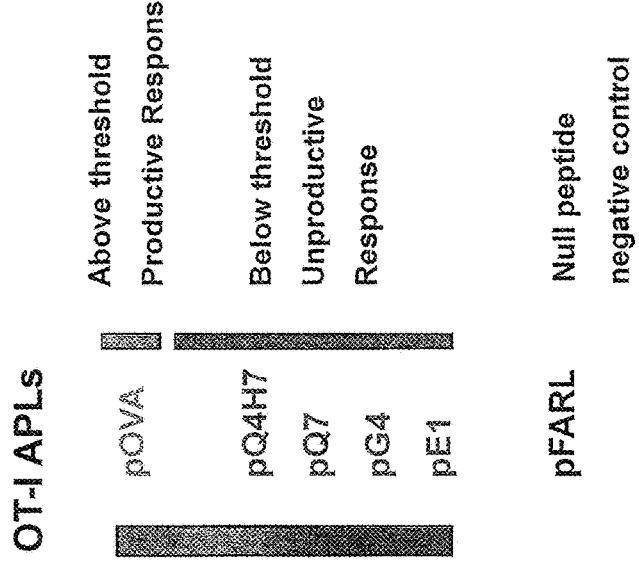
FIG. 14 is a graph listing various altered peptide ligands (APLs) derived from the OVA polypeptide (pOVA) and their levels of immunogenicity.
Figure 15:
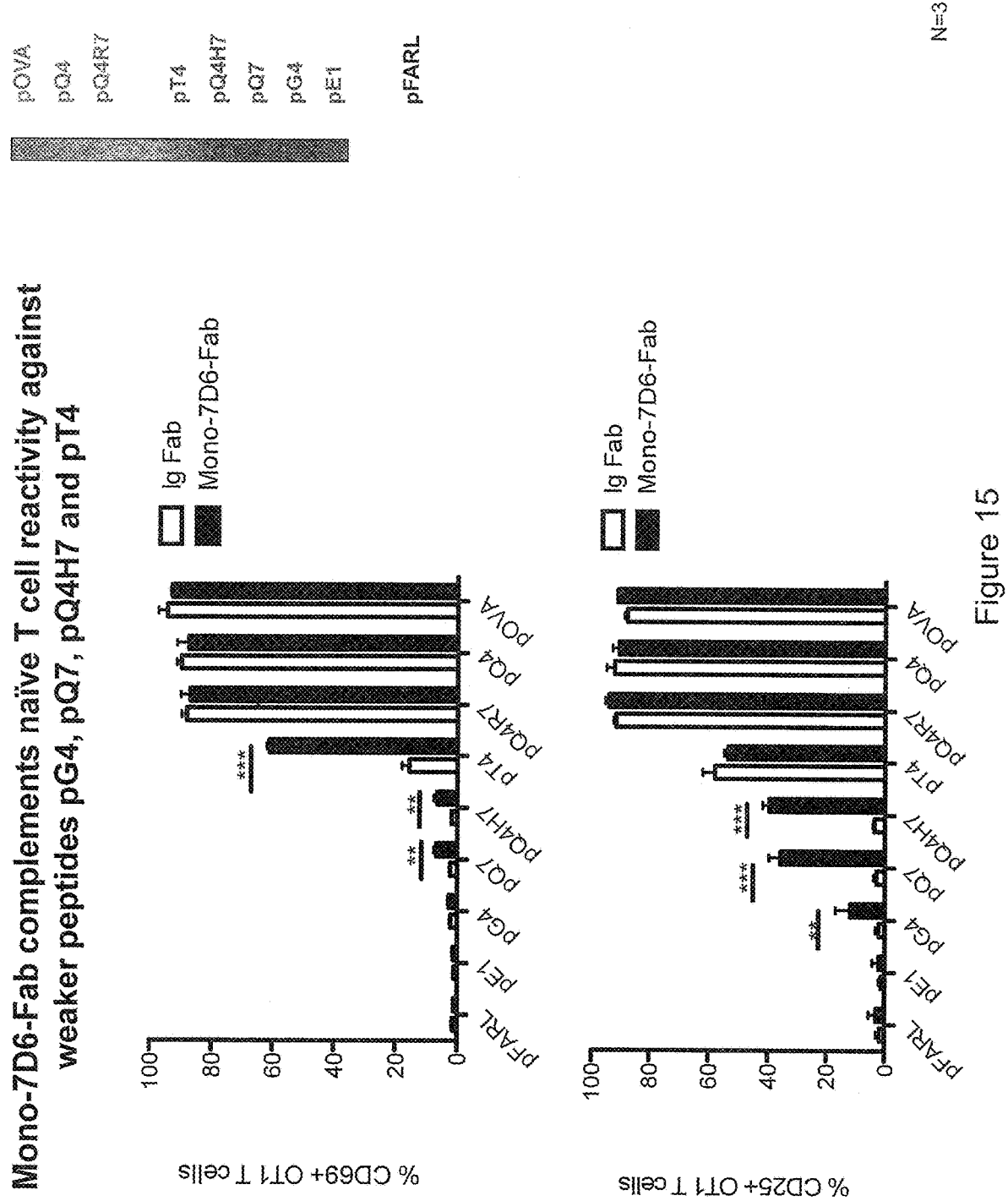
FIG. 15 contains graphs plotting the percent of $CD69^+$ or $CD25^+$ OT-I T cells following exposure to T2-Kb antigen presenting cells (APCs) having H2-Kb MHC—I molecules loaded with the indicated OVA APLs plus either control Fab IgG from mouse (Ig Fab; 5 μg/mL) or Mono-7D6-Fab (5 μg/mL).
Figure 16:
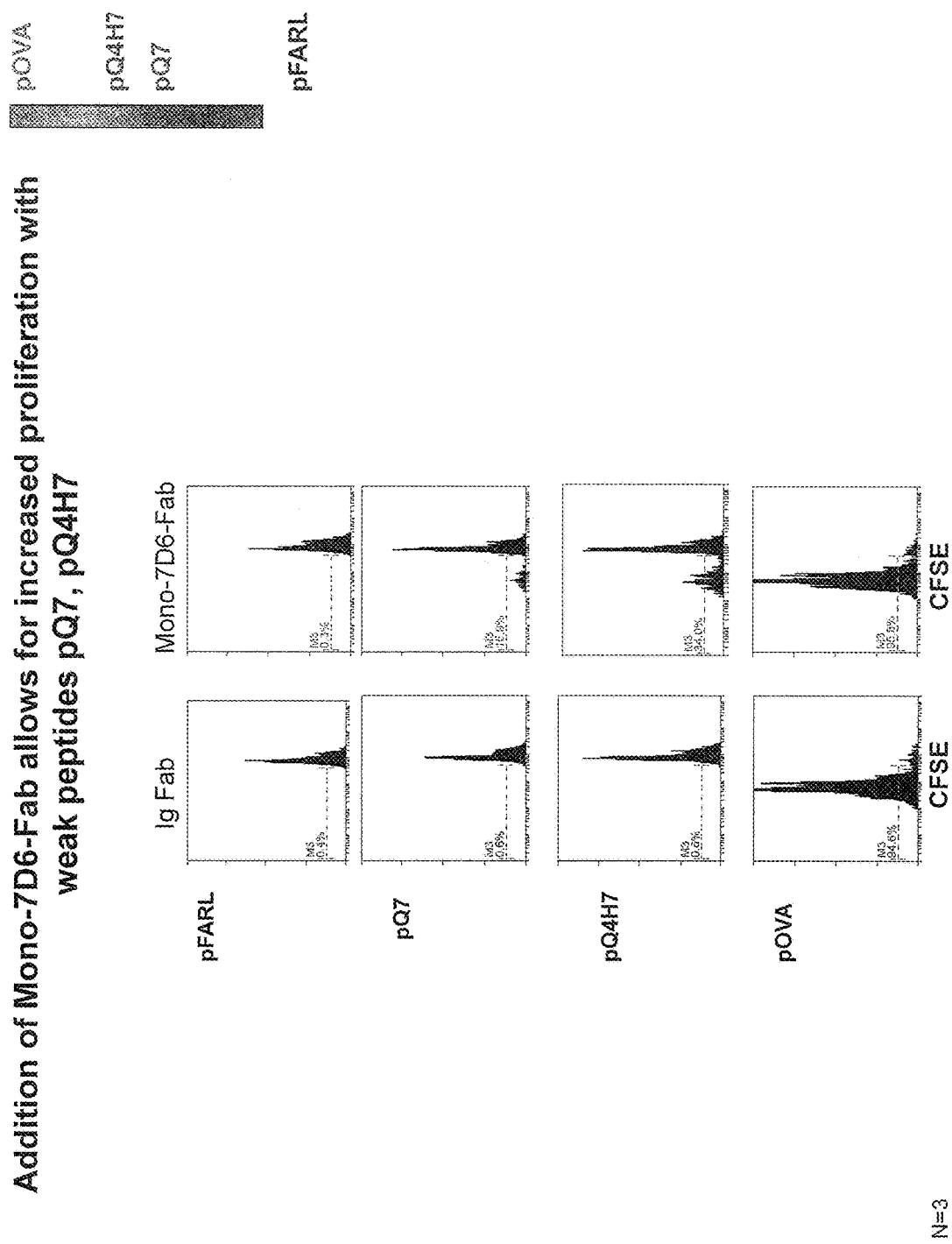
FIG. 16 contains graphs plotting the percent OT-I T cells dividing (M3%) following exposure to T2-Kb antigen presenting cells (APCs) having MHC—I molecules loaded with the indicated OVA APLs plus either control Fab IgG from mouse (Ig Fab; 5 μg/mL) or Mono-7D6-Fab (5 μg/mL).
Figure 17:
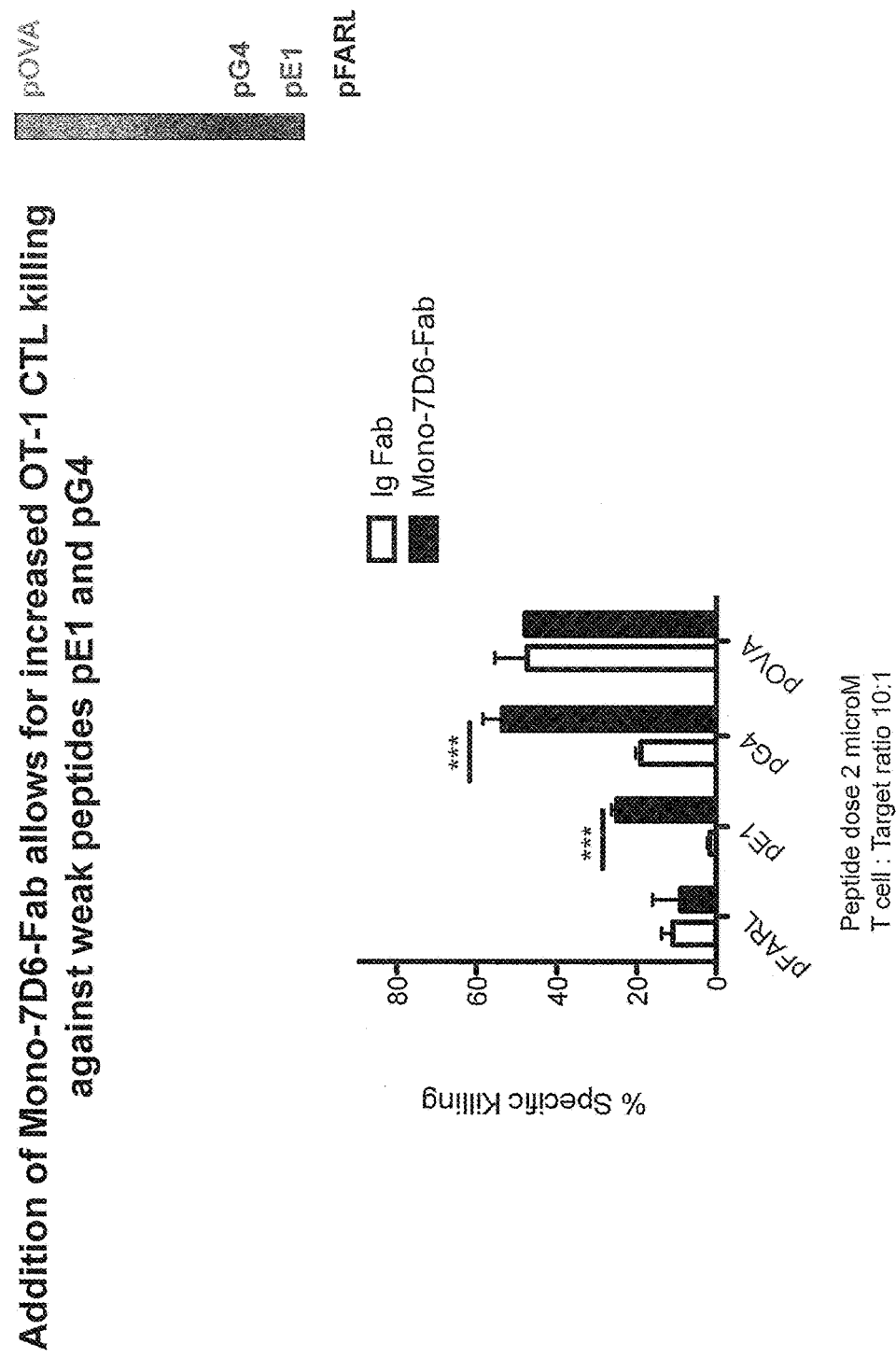
FIG. 17 is a bar graph plotting the percent of OT-I CTL specific killing of EL-4 tumor target cells when incubated in the presence of 2 μM of the indicated OVA APLs with either control Fab IgG from mouse (Ig Fab; 5 μg/mL) or Mono-7D6-Fab (5 μg/mL). The OT-I T cell to target cell ratio was 10:1.
Figure 18:
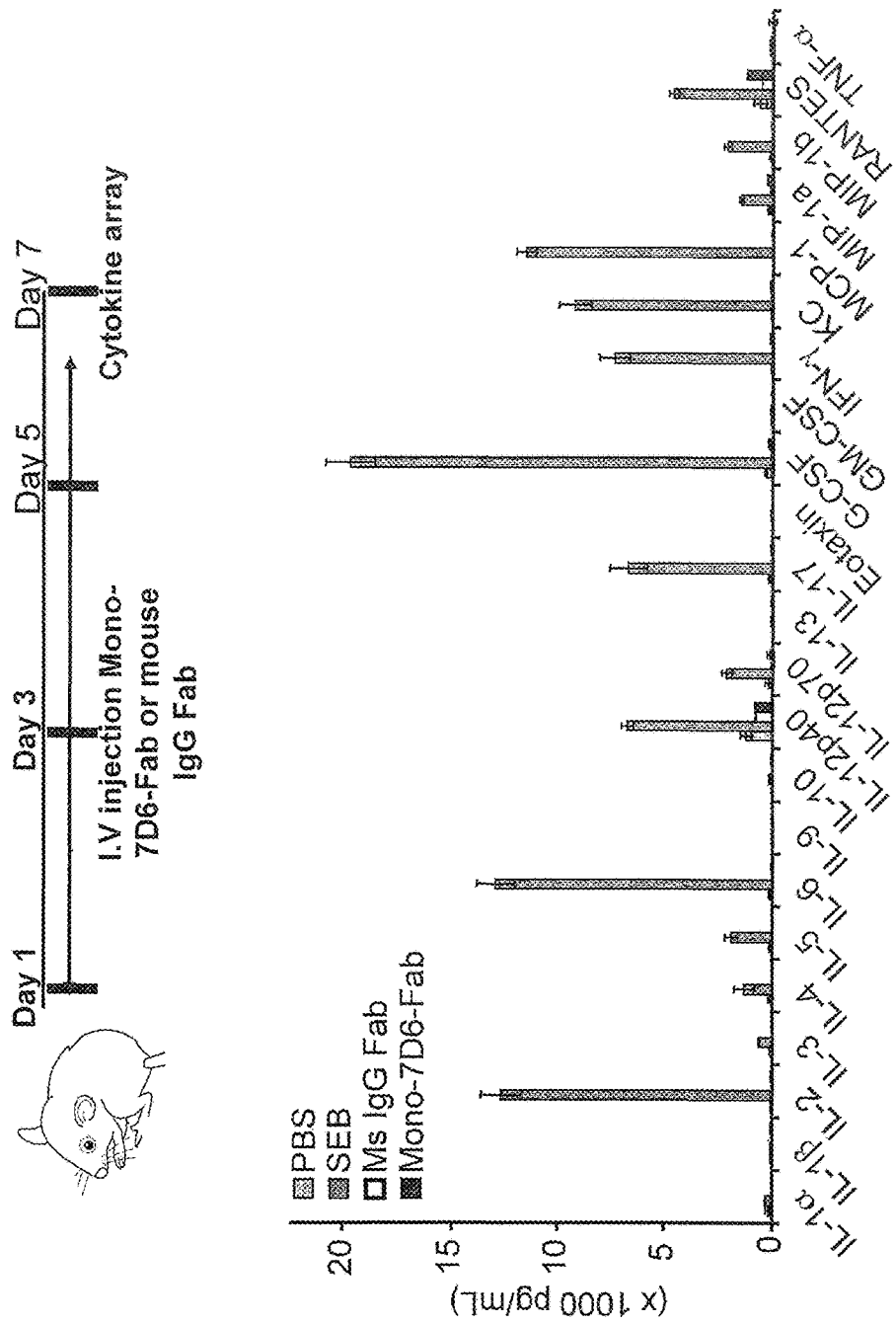
FIG. 18 is a bar graph plotting the levels of indicated cytokines in blood serum from healthy mice at day 7 following intravenous injections of either control Ms Ig Fab; (10 μg/mouse) or Mono-7D6-Fab (10 μg/mouse) on days 1, 3, 5, and 7. Staphylococcal enterotoxin B (SEB) was used as a positive control for an autoimmune response that produces a specific cytokine profile tested in this experiment.
Figure 19:
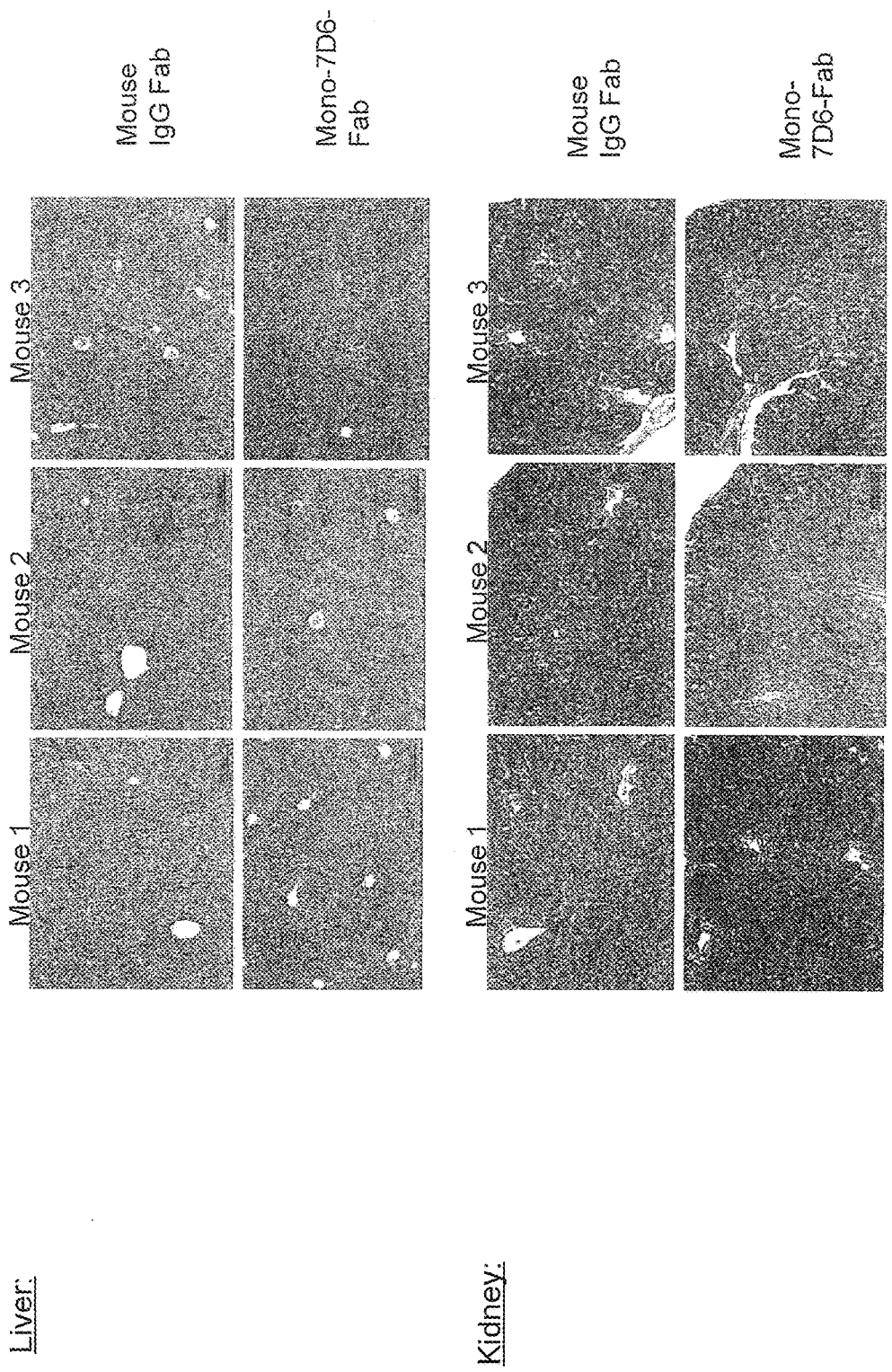
FIG. 19 contains photographs of liver and kidney tissue from the mice tested in FIG. 18 (3 mice injected with Mouse Ig Fab, 10 μg/mouse; or Mono-7D6-Fab, 10 μg/mL) demonstrating that Mono-7D6-Fab does not cause signs of an autoimmune response in the shape of tissue inflammation.
Figure 20:
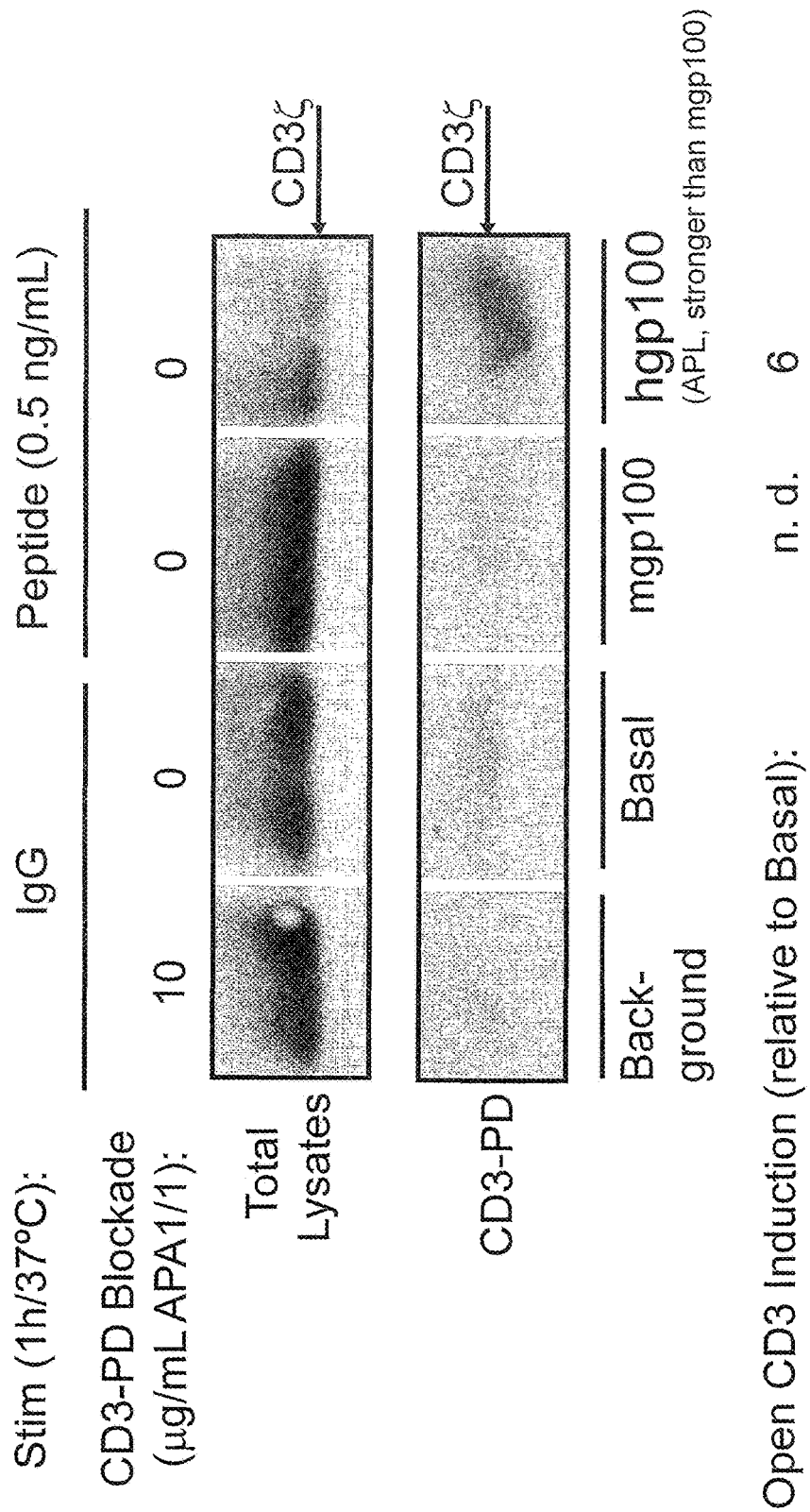
FIG. 20 is a western blot of a CD3 pull down (CD3-PD) assay using Pmel TCR transgenic $CD8^+$ T cells that are specific for the natural/weak tumor antigen mouse gp100 (mg100). Pmel T cells were either treated with a non-specific Ig (Ig) or with the antigens mg100 or hgp100 (xenogeneic variant of mg100 from human melanocytes that functions as a strong antigen for Pmel TCR) for 1 hour at 37° C. Then, Pmel T cells were lysed, and the resulting samples were used to detect CD3 open conformation using the CD3-PD assay as described herein. The western blot revealed that while the strong/xenogeneic variant hgp100 induces CD3Δc (6 fold induction of open-CD3), the weak/natural melanoma antigen mgp100 fails to induce CD3Δc.

Poorly immunogenic antigens failed to stimulate T cells due to their incompetence to induce a conformational change in the CD3 complex (CD3Δc) (FIGS. 6-7). See, also, Gil et al., J. Immunol., 180(6):3900-9 (2008)). The CD3 complex is a group of trans-membrane proteins associated to the T cell antigen receptor (TCR) that are in charge of starting the process of T cell stimulation once the TCR interacts with a given antigen (FIG. 1). The TCR distinguishes the quality of different antigens in order to instruct the activation of immune function. The most upstream marker currently known to be uniformly indicative of T cell stimulatory antigen recognition is CD3Δc (FIG. 2). CD3Δc has the following attributes (FIGS. 2, 5, and 6): (i) it uncovers a cryptic proline rich sequence (PRS) in CD3ε that is a binding site for specific SH3 domains of several cytoplasmic proteins, including Nck; (ii) it is induced by either anti-TCR/CD3 antibodies, anti-CD3 Fab fragments, or antigenic peptide-MHC ligands; (iii) it occurs earlier than (and is independent of) TCR/CD3 crosslinking and src-kinase activity; (iv) when tested as an isolated variable, CD3Δc is required for optimal T cell signaling and immune function. Considering these observations together, CD3Δc marks an initial communication to CD3 that a signaling-relevant peptide/MHC ligand has been bound by TCR. In mature T cells, weak peptide/MHC ligands fail to induce CD3Δc (FIG. 6). See, also, Gil et al., J. Immunol., 180(6):3900-9 (2008)). Most tumor-associated antigens (TAA) are poorly immunogenic and do not stimulated anti-tumor T cell function. It was hypothesized that most natural TAA fail to induce a T cell immune response due to their failure to induce CD3Δc (FIG. 7). Poorly immunogenic TAA from melanoma like mouse gp100, indeed failed to induce CD3Δc (FIG. 20). Mono-7D6-Fab was tested as a means to provide CD3Δc in trans during weak TCR/antigens interactions to increase T cell function triggered by weak/poorly immunogenic antigens. The results provided herein demonstrate that Mono-7D6-Fab is precisely monovalent (FIG. 10), it binds to mouse T cells but does not block peptide/MHC:TCR interactions (FIG. 11), it induces CD3Δc on its own (FIG. 12) (CD3Δc measured by the CD3-PD assay (FIGS. 3-4)), and it is functionally inert to non-antigen engaged T cells both in vitro (FIGS. 13-17) and in vivo (FIGS. 13, 18, and 19). Moreover, the administration of Mono-7D6-Fab enhanced T cell signaling induced by weak peptide/MHC antigens in vitro, as shown in experiments using T cells from the OT-I TCR transgenic mouse model (FIGS. 14-17).

Figure 23:
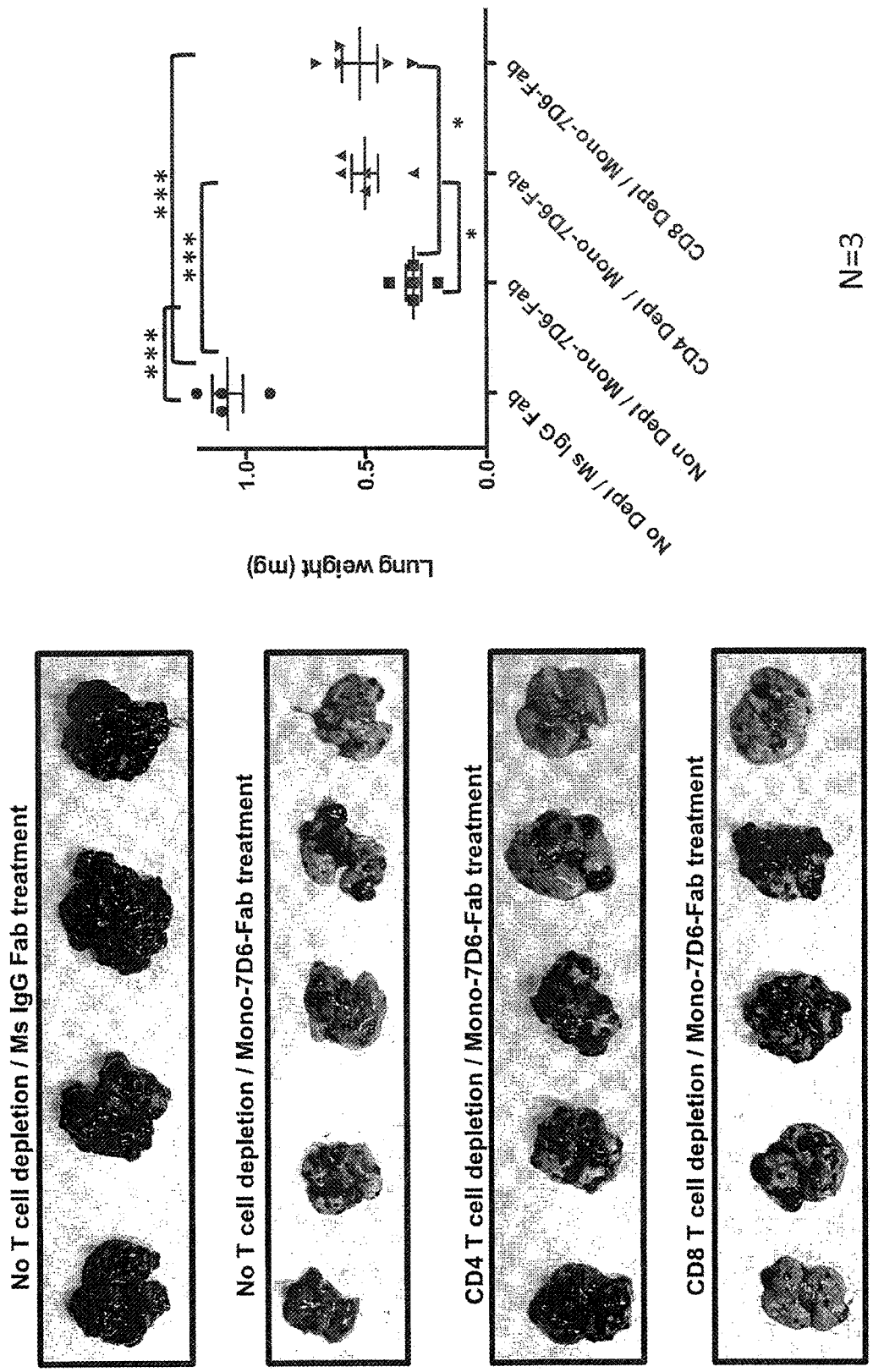
FIG. 23 contains a dot plot to quantify melanoma burden and photographs of lung tissue from mice with T cells (No Depl), without CD4 T cells (CD4 Depl; CD4 T cells were depleted by injecting anti-CD4 specific antibody), or without CD8 T cells (CD8 Depl; CD8 T cells were depleted by injecting anti-CD8 specific antibody) injected with B16.F10 tumor cells on day 0 and treated intravenously with either mouse IgG Fab; (10 μg/mouse on day 0) or Mono-7D6-Fab (10 μg/mouse on day 0). On day 21, the lungs were extracted and evaluated for the presence of metastatic melanoma tumor burden and quantified as descried in FIGS. 21 and 22. The results demonstrate that both CD4 and CD8 T cells are required for the full anti-melanoma effect of Mono-7D6-Fab treatment observed when both CD4 and CD8 T cells are not depleted.
Figure 24:
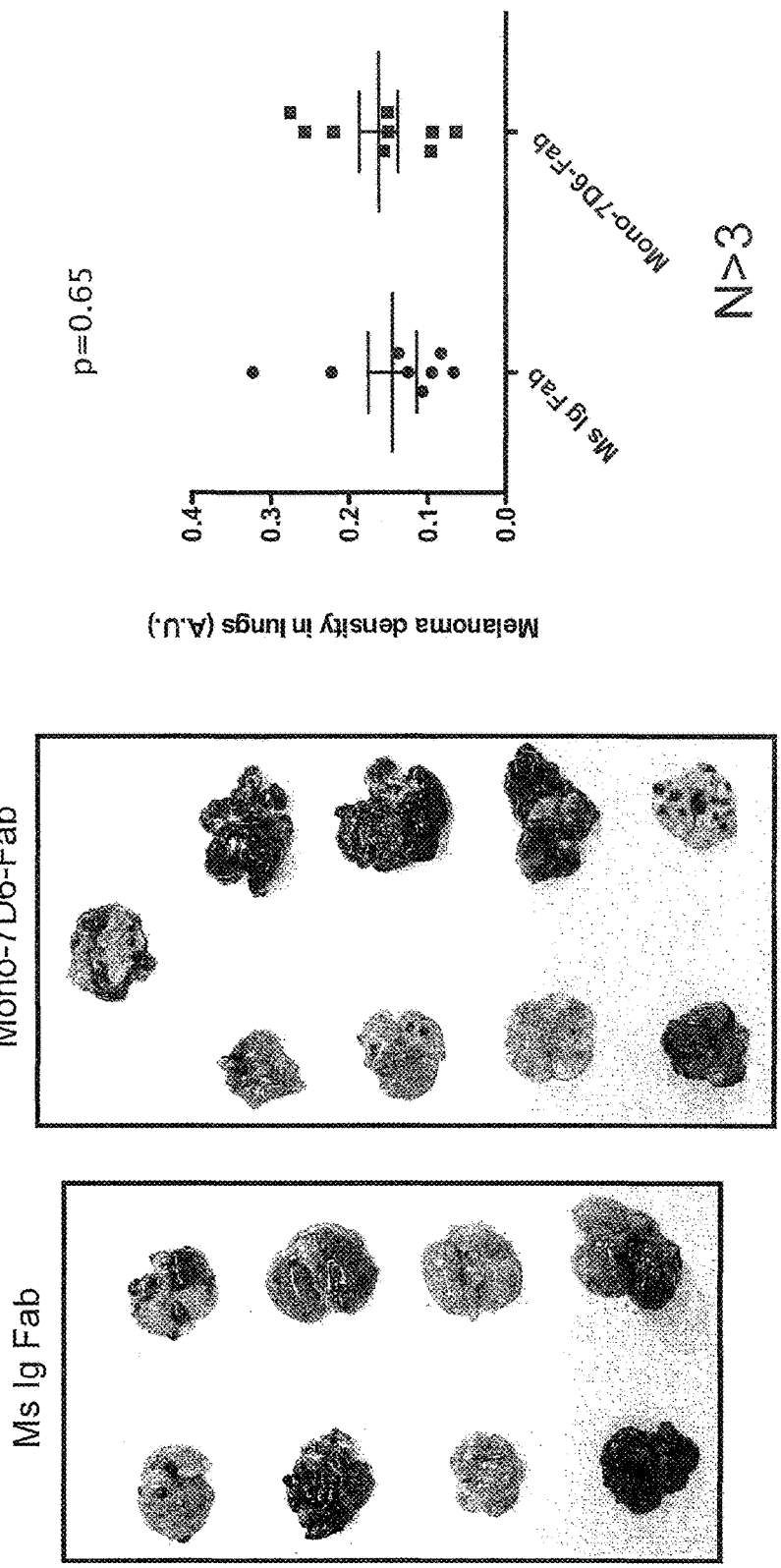
FIG. 24 contains photographs of lung tissue from OT-I Rag2 KO mice. In these mice, the only kind of T cells present are OT-I CD8 T cells specific for an antigen from chicken ovalbumin. Therefore, these T cells are incapable of recognizing any antigens from the B16F10 melanoma tumor. All the OT-I mice were injected with B16.F10 tumor cells on day 0 and treated intravenously with mouse Ig Fab (10 μg/mouse on day 0) or Mono-7D6-Fab (10 μg/mouse on day 0). On day 21, the lungs were extracted and evaluated for the presence of metastatic melanoma tumor burden. Similar tumor burden was observed in both treatment groups, demonstrating that Mono-7D6-Fab treatment requires the presence of CD8 T cells specific for the tumor antigens to exert its anti-tumor effect. On the left, there is an objective quantification of tumor burden in lung of OT-I mice of each treatment group using a dot plot that depicts melanoma density, as specified in FIG. 20. There is not a statistical difference in the melanoma burden between the mouse IgG Fab treated mice and the Mono-7D6-Fab treated OT-I mice.

Mono-7D6-Fab's capacity to increase T cell responses to weak antigens was tested in vivo using a mouse model for lung metastatic melanoma. The B16.F10 cell line is a transplantable melanoma in B6 mice that colonizes lungs when injected intravenously (i.v.). This B16.F10 melanoma line is very aggressive and fast growing in B6 mice, and it is considered poorly immunogenic. In the absence of any specific treatment, T cells from B6 mice fail to mount productive immune responses against the natural TAAs of B16.F10 cells. A single low-dose of Mono-7D6-Fab significantly reduced melanoma burden in the lungs of B6 mice when compared with mouse IgG Fab control treated mice in six different experiments (FIG. 21). Mono-7D6-Fab anti-B16.F10 effects required the presence of T cells in B6 mice (FIG. 22), and both CD4 and CD8 T cells contribute to such effect (FIG. 23). In addition, antigenic specificity of T cells mediating Mono-7D6-Fab is required for Mono-7D6-Fab anti-tumor effects, since in mice lacking T cells specific for B16.F10 Mono-7D6-Fab failed to reduce melanoma burden (FIG. 24). These results demonstrate that Mono-7D6-Fab converted poorly stimulatory mouse TAAs of B16.F10 into efficient stimuli for B16.F10 specific CD4 and CD8 T cells among the natural B6 cell repertoire.

Example 2—Mono-7D6-Fab Promotes Therapeutic Anti-Tumor T Cell Responses in the B16F10/B6 Lung Metastatic Melanoma Model when Administered Three Days After Tumor Injection Mice were injected intravenously with a melanoma cell line (B16F10). Three days later, half of the mice were injected intravenously with a control mouse Fab fragment (Ms IgG Fab) or Mono-7D6-Fab (10 µg/mouse). 21 days after melanoma injection, all mice were sacrificed, and lungs and peripheral lymphoid organs were collected (FIG. 25A). Pictures of the lungs were evaluated for the presence of metastatic melanoma tumor burden. Less melanoma burden was observed in mice treated with Mono-7D6-Fab (FIG. 25B). Lung pictures of each mouse in the experiment were analyzed by a software to quantify melanoma presence. A graph was prepared showing the results of melanoma density in lungs of mice treated with either Ms IgG Fab or Mono-7D6-Fab (FIG. 25C). Melanoma density in each group was statistically different (t test;***p<0.0001), showing a reduced lung metastasis in mice that received Mono-7D6-Fab (FIG. 25C). In addition, T cells were isolated from the lung draining lymph nodes of the mice and stained for different activation markers: CD107a, CD44, and CD62L. Bar graphs were prepared, revealing the % of positive CD4 and CD8 T cells for theses markers (FIGS. 25D and 25E). The results demonstrate an increase in the percentage of CD4 and CD8 T cells being activated in mice receiving Mono-7D6-Fab (FIGS. 25D and 25E).

Example 3—Anti-Melanoma Effect when Mono-7D6-Fab Therapy is Combined with Adoptive Transfer of Melanoma Specific Cytotoxic Lymphocytes Mice were injected intravenously with the melanoma cell line (B16F10). Three days later, half of the mice were injected intravenously with a control mouse Fab fragment (Ms IgG Fab) or Mono-7D6-Fab (10 µg/mouse). In addition, mice were injected at the same time with cytotoxic T lymphocytes (CTLs) and IL-2. IL-2 administration was repeated on days 4 and 5. The CTLs were either non-tumor specific (OT-I CTLs) or tumor specific (Pmel-1 CTLs). 28 days after melanoma injection, all mice were sacrificed, and lungs and peripheral lymphoid organs were collected (FIG. 26A). Pictures of the lungs were evaluated for the presence of metastatic melanoma tumor burden (FIG. 26B). In addition, lung pictures of each mouse in the experiment were analyzed by software to quantify melanoma presence (FIG. 26C). The results of melanoma density in lungs of mice in the four experimental groups generated in the experiment (Ms IgG Fab/OT-I CTLs, Mono-7D6-Fab/OT-I CTLs, Ms IgG Fab/Pmel-1 CTLs, and Mono-7D6-Fab/Pmel-1 CTLs) were graphed (FIG. 26D). Statistical analysis of melanoma density indicates that there was a synergistic effect against melanoma when Mono-7D6-Fab was combined with the Pmel-1 CTLs specific for the tumor but not when combined with the non-tumor specific OT-I CTLs (t test, *p<0.005p<0.001*p<0.0001). CD8 T cells present in the mediastinal lymph node (FIG. 26D) or the lungs (FIG. 26E) of the mice engaged in this experiment were stained with the Kd-tetramer gp100 to identify cells specific for the melanoma antigen gp100. The bar graphs revealed the increase in CD8 T cell counts specific for the melanoma in the mice receiving the Mono-7D6-Fab (FIG. 26D).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing an immune response against an antigen, wherein said method comprises:
    administering a composition comprising
        a monovalent anti-CD3γε antibody preparation and said antigen or nucleic acid that expresses said antigen to a mammal,
    wherein said monovalent anti-CD3γε antibody preparation comprises Fab fragments of an anti-CD3γε antibody that specifically binds to a CD3 dimer but does not bind to a CD3γε polypeptide alone or a CD3ε polypeptide alone, induces a conformational change in a CD3 complex (CD3Δε), does not stimulate T cells on its own, does not block interaction of T cell receptor with the antigen, and does not block T cell response to the antigen and
    wherein said mammal produces an immune response against said antigen that is increased as compared to an immune response produced against said antigen when said antigen or said nucleic acid is administered to a comparable mammal in the absence of said monovalent anti-CD3γε antibody preparation.

2. The method of claim 1, wherein said mammal is a human, and said Fab fragments are Fab fragments of an anti-human CD3γε antibody.

3. The method of claim 1, wherein said Fab fragments are Fab fragments of a humanized anti-human CD3γε antibody.

4. The method of claim 1, wherein said Fab fragments are Fab fragments of a fully human anti-human CD3γε antibody.

5. The method of claim 1, wherein said antigen is a tumor associated antigen.

6. The method of claim 5, wherein said tumor associated antigen is a polypeptide.

7. The method of claim 1, wherein said antigen is within an extract from a whole tumor cell lysate.

8. The method of claim 1, wherein said method comprises administering said antigen to said mammal.

9. The method of claim 1, wherein said method comprises administering said nucleic acid to said mammal.

* * * * *